United States Patent [19]
Cherry et al.

[11] Patent Number: 5,879,921
[45] Date of Patent: Mar. 9, 1999

[54] RECOMBINANT EXPRESSION OF A GLUCOSE OXIDASE FROM A CLADOSPORIUM STRAIN

[75] Inventors: Joel R. Cherry; Randy M. Berka, both of Davis, Calif.; Torben Halkier, Birkeroed, Denmark

[73] Assignees: Novo Nordisk A/S, Bagsvaerd, Denmark; Novo Nordisk Biotech, Inc., Davis, Calif.

[21] Appl. No.: 746,257

[22] Filed: Nov. 7, 1996

[51] Int. Cl.[6] .............................. C12N 9/04; C12N 15/09; C12N 15/53
[52] U.S. Cl. ................... 435/190; 435/320.1; 435/252.3; 435/254.11; 435/254.7; 435/6; 536/23.7; 536/24.3
[58] Field of Search ................................ 435/190, 320.1, 435/6, 252.3, 254.11, 254.7; 536/23.2, 24.3

[56] References Cited

FOREIGN PATENT DOCUMENTS

WO 95/29996  11/1995  Denmark .......... C12N 9/04
WO 89/12675  12/1989  U.S. .................. C12N 1/16

OTHER PUBLICATIONS

Suggs et al. "Use of synthetic oligonucleotides as hybridization probes: Isolation of cloned cDNA sequences for human beta2–microglobulin" (Nov. 1, 1981) Proc. Natl. Acad. Sci. USA vol. 78, No. 11, pp 6613–6617.

*Primary Examiner*—Robert A. Wax
*Assistant Examiner*—Bradley S. Mayhew
*Attorney, Agent, or Firm*—Steve T. Zelson; Elias J. Lambiris; Robert L. Starnes

[57] ABSTRACT

The invention is directed to alkaline glucose oxidases comprising novel peptide sequences. Furthermore, the invention relates to methods for producing and using said glucose oxidases.

25 Claims, 9 Drawing Sheets

FIG. 2A

```
  L   A   A   A   V   P   L   K   L   A   S   P   N   V   G   K   N   M   Q   E   Q   T   K   N   T   L   W   F   Q
CCGTCAACACCGAGTTCGATGGTTCTCGGACCACCAAGGCCCATCTCTTCCGAATGTCAGTTGTTCAGGAATAACAGCGCCACCA 1530
  P   V   N   T   E   F   Q   G   S   G   P   P   N   A   I   S   F   P   N   V   D   Q   L   F   R   N   N   S   A   T
TGTACAAGAACATCATGTCTGGCCTCAAGCAATACTCAGAAGACCTGGCCGTACCGGCACGTGACCAACGCCACAGCCACCAGA 1620
  M   Y   K   N   I   M   S   G   L   K   Q   Y   S   F   Q   I   A   A   T   G   V   T   N   A   T   A   T   H   Q
TCCTCGAAGCACAGGTCGACAACCTCTGGCACAACCTGTAGGGCCACCGGAAATCTTCTGACATCACCCGCCACCGGCCAAGTCG 1710
  I   F   A   Q   V   D   N   I   W   H   N   I   V   G   A   A   F   I   F   F   V   T   S   P   A   T   G   Q   V
GCCTCAGCCCTCGGAACCTGATCGTTTTGTCCGTGGCTATGTGCACATCCTCAAACTCCTCATGGGATCACCCAGAAATCGAGCCTT 1800
  G   V   D   I   W   N   L   I   V   L   S   R   G   Y   V   H   I   T   S   N   S   S   W   D   H   P   E   I   E   P
CCTACTTCGGTCACCAATTCGACCTCGACGTCGCCAACTAGCAGCCAAGCAGTCTTCCAGACCGACCCTCTAGCTCCTC 1890
  S   Y   F   G   H   Q   F   D   L   D   V   Q   L   A   A   T   K   Q   S   R   E   V   F   Q   T   D   P   L   A   P
TCGTCAGCGCTGAGACTTTCCCGGGCCTTGAAGCCTGCCCAAGGCCAGAATCAGGTCTCGGAGCAGTGGTCAAAGCCACCTTCA 1980
  L   V   S   A   E   T   F   P   G   L   E   A   V   P   Q   G   A   E   D   Q   V   W   E   Q   W   V   K   A   T   F
CCTCTGTCTGGCACTACATCGGCAACCTTGGGCTATGATGAAGGAGGAACTTGGAGCCGGTCCTGGACACAGATTGAAGGTCTACGGTATTG 2070
  T   S   V   W   H   Y   I   A   T   I   G   M   K   E   E   L   G   G   V   Q   S   R   L   K   V   Y   G   I
AGAATGTGCGTGCTGTGGATGCTAGCGTGTTGCCGATTCAGCTTTCGGGCCATTCTTAGTCTTCGGCTATGGCATTGCTGAGAAGGCTG 2160
  E   N   V   R   A   V   D   A   S   V   L   P   I   Q   L   S   A   H   L   S   S   L   Y   G   I   A   E   K   A
CGAAGATGATCAAGGAGGATCAGAGGGCCTGATTAGCGTTCTAAAAACAATCATGATAGCATGTTTGAGTGCATCTCATTGCAGCTCTG 2250
  A   K   M   I   K   E   D   Q   R   A
GGCGGAATTTTGTGGCTCTGCTAATAAGGAGTCCTTGGCTTAAGTATGCACTCACACCAACATTTTATCTACATCGCTTAGTAGGCATGA 2340
TGTACGAATCCACATCCAATCAGTCCTATCATCGTATAAGTCTGTC 2386
```

FIG.2B

```
LIPMAN-PEARSON PROTEIN ALIGNMENT
KTUPLE: 2:     GAP PENALTY: 4:    GAP LENGTH PENALTY: 12

SEQ1 (1>614)        SEQ2 (1>605)          SIMILARITY    GAP       GAP      CONSENSUS
C. OXYSPORUM GOX    A. NIGER GOO          INDEX         NUMBER    LENGTH   LENGTH
(3>610)             (2<600)               31.7          13        17       612 v10        v20        v30        v40        v50        v60        v70        v80
YKPIALSTLLAVASQALPHQSRAESAHA--ITAQYSQVSNKTFDYIVCGGGLTGLVVASRLSEDPNISVLVIEGGN--QOHEDPRVNQVRTY
 :: :::  ::::  :  :  :: :::   :  : :   ::::  :::   ::::::::::::::::::::::::   ::::::::::  :
MQTLLLVVSLAAALPHYIRSNGIEASLLTQPKQVSGRTVDYIIAGGGLTGLTTAARLTENPNISVLVIESGSYESORGPIIEDLNAY
                                                                    fff    1   1    2
          -10        -20        -30        -40        -50        -60        -70        -80        -90
v90       v100       v110       v120       v130       v140       v150       v160       v170
GQAFETELOYGLXSTSVPWQNNTGLLLVAGKTILGGSGSINGASWTKGOXTQYDLLPGLTGOOSWSFDALNEIMLSIEDFHTPIEDQVAKG
 :: :::  ::    : : : : :: : :  :::::   :::   :::: :  : ::: :::  : : :: : : :: : ::   :: 
GDIFGSSVDHAYETVELATNNQTALI--RSGNGLGGSTLVNGGTWTRPHKAQVDSWETVFGNEGWNWDNYAAYSLQAERARAPNAKOIAAG
        3f                f ff  ff f 4 f            f                             4        5
          -100       -110       -120       -130       -140       -150       -160       -170
v180      v190       v200       v210       v220       v230       v240       v250       v260
AAFEGEFHGREGNVQVSFPAGMFGSIQQPALEASALVWKGMKKVADFAAGITTGATMIPNMLEANESQNRSSPFTVYYAKQQTQERONFII
 : :  ::: :  ::  ::    : :  :: :::: :: :: : ::   :  ::  : ::   ::  :: : :::    ::::    :  
HYFNASCHGVNGTVHAGPROTGOOYSPIVKALMSAVEDRGVPTKKDFGCGOPHGVSMFPNTL--HEDQVRSQAAREWLLPNYQ-RPNLQV
        5                                                                                 ff
-180      -190       -200       -210       -220       -230       -240       -250       -260
v270      v280       v290       v300       v310       v320       v330       v340       v350
```

FIG.3A

```
LTGHRV-ISLNWREGSEMIADGVSFQACRQCKIHKAKTKREVLLAGGSLQSPQLLELSGVGNPQVLAAAAVPLKLASPNVGKNMQEQTKN
||| |    ::|:  |||  ||| :|: :|:. |||||||: ||.::||::|:| || :||| ::|:. |:|:.  ::: |:|:||:.
LTGQYVGKVLLSQNGTTPRAVGVEFGTHKG-NTHNVYAKHEVLLAAGSAVSPTILEYSGIGMKSILEPLGIQTVVDLP-VGLNLQDDQTTA
-270        -280        -290        -300        -310        -320        -330        -340
v360        v370        v380        v390        v400        v410        v420        v430
fff fff                                 ffff       fffff  f6ffff f6ffff TLWFDPVNTEFDGSGPPNAISFPNVDOLFRNNSATMYKNIMSGLKQYSEDLAATGTVTNATATHQILEAQVQNLWHNLVGAAEIFFVTSP
|::  ::::.   : |: |:::.|::    ||:  ||  :||||  :|:  |:  ||| ||:   |::|:|  |: ||:|   :||:|:|
TVR-SRITSA-—CAGQGQAAWFATFNETFGDYSEKAHELLNTKLEQWAEEAVARGGFHNTTALLIQYENYRDWIYNHNVAYSELFLDT——
-360        -370        -380        -390        -400        -410        -420        -430
v450        v460        v470        v480        v490        v500        v510        v520
                                                7     7                              8

ATGQVGVDDLWNLIVLSRGYVHITSNSSW-QHPEIEPSYFGHQFQLQVQLAATKQSREVFQTQPLAPLVSAETFPGLEAVPQGAEDQWWEO
 :| :::||::|| |:|:|:  : | |     ||  :::| | :| :| |||::|: | | |  :|:|||  |:.:|::: |: :.|| 
-AGVASFDVWDLLPFTRGYVHILQKDPYLHHFAYDPQYFLNELQLLGQAAATQLARNISNSGAMQTYFAGETIPG-DNLAYDAQLSAWTE
-440        -450        -460        -470        -480        -490        -500        -510        -520
v540        v550        v560        v570        v580        v590        v600        v610
        9                    10  10            6                     8
                             11                12                                    11
                                                                                      12

WYKAITFTSVWHYIATLGMMKEELGGVVQSRLKVYGIENVRAVDASVLPIQLSAHLSSSLYGIAEKAAKMIKEDQRA
::||:|||:|:|: |:|:||  ||::::|||:|::|| ::| :|:||:|||:: |:::|||:|  ||::||::|:.
YIPYHFRPNYHGVGTCSMMPKEMGGVVQNAARVYGVQGLRVIQGSIPPTQMSSHVMTVFYAMALKISDAILEDYASM
-530        -540        -550        -560        -570        -580        -590        -600
        9
```

FIG.3B

RECOMBINANT EXPRESSION OF A GLUCOSE OXIDASE FROM A CLADOSPORIUM STRAIN

1. FIELD OF INVENTION

The present invention relates to polypeptides having glucose oxidase activity as well as nucleic acid fragments comprising nucleic acid sequences encoding said glucose oxidases. This invention also relates to nucleic acid constructs, vectors, and host cells comprising the nucleic acid sequences, as well as methods for producing and using said glucose oxidases.

2. BACKGROUND OF THE INVENTION

Glucose oxidases are enzymes that catalyze the oxidation of glucose with oxygen whereby D-gluconic acid and hydrogen peroxide are formed. Such enzymes are known from microbial, plant and animal origins, e.g., glucose oxidase from Aspergillus, Penicillium and Talaromyces. Glucose oxidase has been described as useful for various purposes, e.g., for bleaching purposes and in the baking industry, useful for strengthening the dough.

An example of a commercial glucose oxidase is Gluzyme™, an *Aspergillus niger* glucose oxidase, available from Novo Nordisk A/S. The glucose oxidase from *A. niger* has been reported to have a molecular weight of about 150,000 and an FAD content of 2 FAD/mole. This enzyme has been cloned and expressed in a recombinant nucleic acid system (U.S. Pat. No. 5,094,951). This and similar products from other commercial sources have an acidic pH optimum, typically around pH 5, which means that they are not very active in detergent solutions or in baking due to the alkaline character of the detergents and baking processes.

A glucose oxidase with a neutral pH optimum has been isolated from strains of Cladosporium (WO 95/29996). This property makes the glucose oxidase particularly effective in detergent applications and in baking processes. However, no significant amino acid sequence analysis nor recombinant production of this enzyme has been accomplished. It would be advantageous to be able to isolate large quantities of such a glucose oxidase. Such a goal may be accomplished via recombinant methods of production.

3. SUMMARY OF THE INVENTION

The present invention relates to isolated polypeptides having glucose oxidase activity selected from the group consisting of:

(a) a polypeptide obtained from a strain of Cladosporum or a synonym or teleomorph thereof which has more than about 75% of maximum activity between about pH 5–8, determined at about 30° C. with D-glucose as substrate;

(b) a polypeptide which has an amino acid sequence depicted which has at least about 50% identity with the amino acid sequence set forth in SEQ ID NO:1;

(c) a polypeptide which is encoded by a nucleic acid sequence which is capable of hybridizing under medium stringency conditions with the nucleic acid sequence set forth in SEQ ID NOS:2 or 3, (ii) its complementary strand, or (iii) a subsequence of (i) or (ii); and (d) an allelic form or fragment of (a), (b) or (c).

As defined herein, an "isolated" glucose oxidase is a glucose oxidase which is essentially free of other non-glucose oxidase proteins, for example, at about 80% pure, most preferably about 90% pure, and even most preferably about 95% pure, as determined by SDS-PAGE.

"Obtained from" as used herein in connection with a given source shall mean that the polypeptide is produced by the source or by a cell in which a gene from the source has been inserted.

The invention is also related to nucleic acid fragments comprising nucleic acid sequences encoding said glucose oxidases shown in SEQ ID NO:2 or 3, SEQ ID NO:2 (DNA+amino acid sequence) is shown in FIG. 2 and depicts SEQ ID NO:3 (DNA+amino acid sequence) depicts the nucleic acid sequence corresponding to the coding region of said glucose oxidase, or nucleic acid subsequences thereof encoding a polypeptide subsequence having substantially the same activity as said glucose oxidase. Additionally, this invention relates to nucleic acid constructs, vectors, and host cells comprising the nucleic acid sequences.

The invention further relates to a method for producing said glucose oxidase as well as the glucose oxidase obtained from said method. In one embodiment, said glucose oxidase may be produced by (a) fermenting a Cladosporium strain to produce a supernatant comprising the glucose oxidase; and (b) recovering the glucose oxidase.

In another embodiment, the glucose oxidase may be produced by (a) fermenting a host cell comprising a nucleic acid construct comprising a nucleic acid sequence encoding said glucose oxidase under conditions conducive to the expression of the glucose oxidase; and (b) recovering the glucose oxidase.

The invention further relates to methods of and compositions for using the glucose oxidase obtained according to the method of the present invention. In the baking industry, the glucose oxidase of the present invention may be added to dough in an amount effective to strengthen gluten quality in dough. In the personal care area, the glucose oxidase may be added to toothpaste, in particular, whitening teeth, mouthwash, denture cleaner, liquid soap, skin care creams and lotions, hair care and body care formulations and solutions for cleaning contact lenses in an amount effective to act as an antibacterial agent The glucose oxidase of the present invention may also be a component of a laundry detergent composition or a dishwashing detergent composition and may be used as a hydrogen peroxide source. The laundry detergent composition may comprise a surfactant, said glucose oxidase, and a substrate for the glucose oxidase. The dishwashing detergent composition may comprise said glucose oxidase and a bleach precursor or peroxy acid, and substrate for glucose oxidase. Said glucose oxidase may particularly be useful for removing stains.

4. BRIEF DESCRIPTION OF DRAWINGS

The present invention is further illustrated by reference to the accompanying drawings, in which FIG. 1 shows the relation between pH and the glucose oxidase activity of glucose oxidase according to the invention, with D-glucose as substrate in the presence of oxygen at 30° C., using a buffer system adjusted to predetermined pH values of from pH 4 to pH 9.

FIG. 2 shows the DNA sequence (SEQ ID NO:2) and deduced amino acid sequence (SEQ ID NO:1) of *Cladosporium oxysporum* glucose oxidase. Amino acid sequences corresponding to peptides previously sequenced are underlined. N-linked glycosylation sites are marked (*), and putative promoter "CAAT" and "CATAA" boxes and polyadenylation signal "AAACAA" are boldfaced.

FIG. 3 shows the alignment of *C. oxysporum* (top) (SEQ ID NO:29) and *A. niger* (bottom) (SEQ ID NO:30) glucose oxidase peptide sequence. Identical residues are connected by lines, homologous residues are connected by dots. Residues forming hydrogen bonds to the FAD cofactor in the *A. niger* enzyme are underscored with "f" while residues involved in intramolecular salt bridges in the *A. niger* enzyme (H. J. Hecht et al., 1993, J. Mol. Biol. 229:153–172) are numbered as pairs 1 through 12.

5. DETAILED DESCRIPTION OF THE INVENTION

5.1. Isolation of the Glucose Oxidase

5.1.1. The Microorganism

Figure 1:
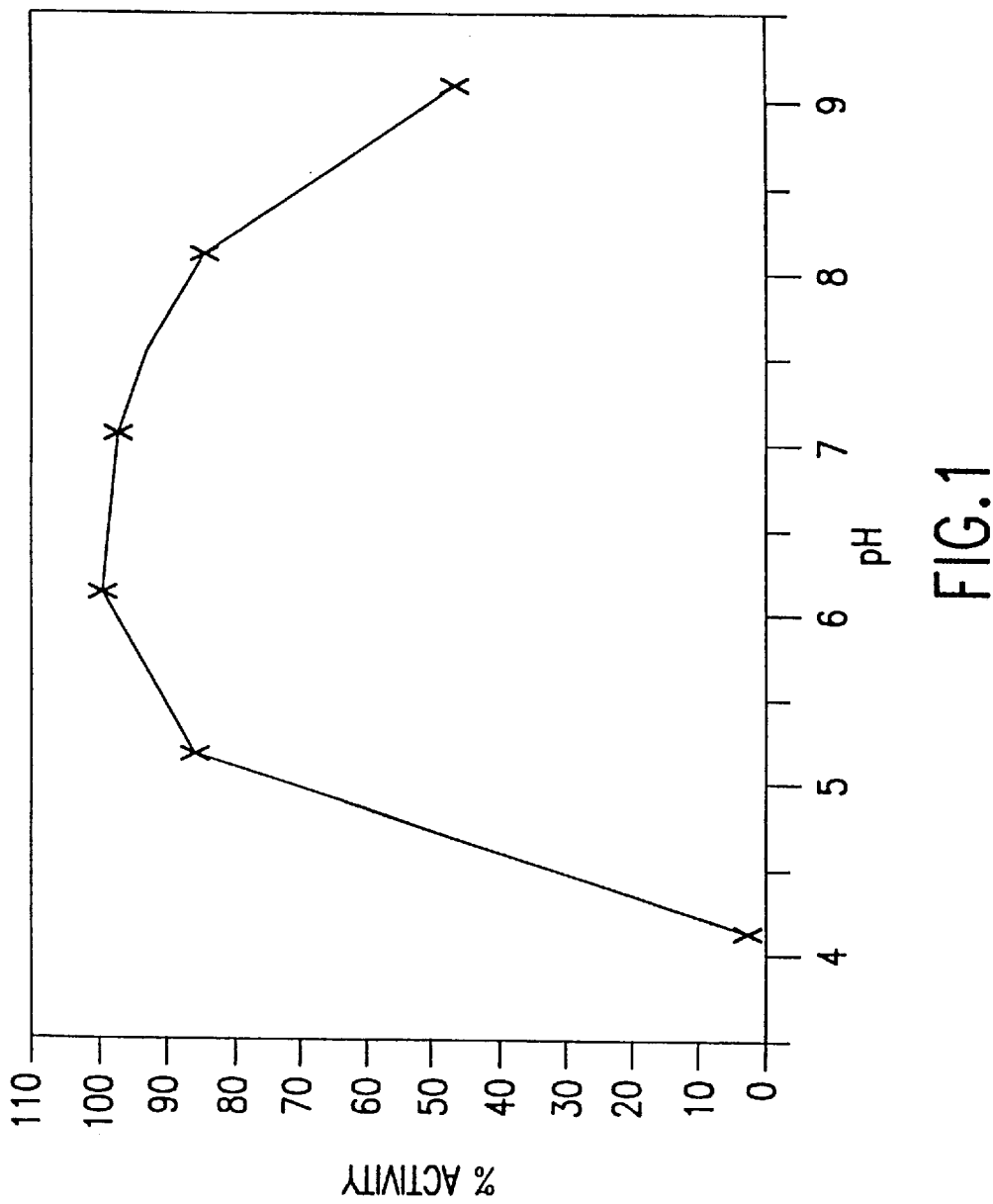

The polypeptides having glucose oxidase activity may be obtained from microorganisms which are synonyms of Cladosporium as defined by Ellis, MB, *Dematiaceous Hyphomycetes,* Commonwealth Mycological Institute, Kew, England, 1971 or teleomorphs of Cladosporium as described in Ellis, MB, *Dematiaceous Hyphomycetes,* Commonwealth Mycological Institute, Kew, England, 1971. Synonyms of Cladosporium which include but are not limited to Sporocladium, Myxocladium, Didynotrichium, Heterosporuim are readily accessible to the public in a number of culture collections, such as the American Type Culture Collection (ATCC), Deutsche Samnmlung von Mikroorganismen und Zellkulturen GmbH (DSM), Centraalbureau Voor Schimmelcultures (CBS), and Agricultural Research Service Patent Culture Collection, Northern Regional Research Center (NRRL). Known teleomorphs of Cladosporium include *Cladosporium echinulatum* or *Heterosporium echinulatum.* Strains of Cladosporium and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The genus Cladosporium is characterized primarily by the formation of conidia in branching chains, which are very fragile and readily break up into units. The conidia can be either hyaline or pigmented, smooth or roughened, continuous or septate. The conidiophores are erect and pigmented, branching irregularly at the apex. *Cladosporium oxysporum* is further described by M. B. Ellis in *Dermatiaceous Hyphomycetes,* 1971, p. 312, CAB International, UK.

A strain representative of *Cladosporium oxysporum* has been deposited according to the Budapest Treaty on the International Recognition of the Deposits of Microorganisms for the Purpose of Patent Procedures, on 25 Mar. 1994, at Centraalbureau voor Schimmelcultures (CBS), under Accession No. CBS 163.94.

5.1.2. Production

Polypeptides having glucose oxidase activity may be produced by fermentation of the above mentioned microbial strain on a nutrient medium containing suitable carbon and nitrogen sources and inorganic salts, using procedures known in the art (see, e.g., Bennett, J. W. and LaSure, L. (eds.), *More Gene Manipulations in Fungi,* Academic Press, Calif., 1991). Suitable media are available from commercial suppliers or may be prepared according to published compositions (e.g., in catalogues of the American Type Culture Collection). A temperature in the range of from 20° C. to 30° C. is suitable for growth and glucose oxidase production.

As defined herein, the term "fermentation" is any method of cultivation of a cell resulting in the expression or isolation of said polypeptides. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the glucose oxidase to be expressed or isolated.

The resulting polypeptides have glucose oxidase activity produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

5.1.3. Assay for Glucose Oxidase Activity

Glucose oxidase activity is determined in the following way: Glucose oxidase oxidizes D-glucose in the presence of oxygen producing D-gluconic acid and hydrogen peroxide. The hydrogen peroxide formed, in the presence of peroxidase, oxidizes ABTS (2,2'-azinobis(3-ethylbenzothiazoline-6-sulfonate)). The greenish-blue colour resulting after a fixed reaction time measured as the absorbance at 418 nm is a function of the amount of hydrogen peroxide. The activity of glucose oxidase is given in UNITS (1 UNIT is the amount of glucose oxidase which under the above standard conditions forms 1 $\mu$mole of hydrogen peroxide per minute).

5.2. The Glucose Oxidase

5.2.1. Physico-chemical Properties of the Glucose Oxidase

Polypeptides having glucose oxidase activity possess the following properties:

A pH profile as shown in FIG. 1, is determined at about 30° C. in the pH range of from pH 4 to pH 9. The assay for glucose oxidase activity described above is run in a buffer of $CH_3COOH$, $KH_2PO_4$ and $H_3BO_3$ at a glucose level of 100 mM. The reaction time is 20 minutes. The peroxidase reaction is run separately after the incubation of the glucose oxidase. It appears from FIG. 1 that the enzyme possesses glucose oxidase activity from approximately pH 4 to above pH 9, having more than about 75% of maximum activity at about pH 5–8, and preferably having an optimum in the range of about 6–7.

Polypeptides having glucose oxidase activity will have an amino acid sequence depicted in SEQ ID NO:1 or having a degree of identity of at least about 50%, preferably about 60%, more preferably about 70%, yet more preferably about 80%, even more preferably about 90%, even yet more preferably about 95%, and most preferably about 97%, which qualitatively retain the activity of the glucose oxidases (hereinafter "homologous glucose oxidases"). In a preferred embodiment, the homologous glucose oxidases have an amino acid sequence which differs by five amino acids, preferably by four amino acids, more preferably by three amino acids, even more preferably by two amino acids, and most preferably by one amino acid from the amino acid sequence set forth in SEQ ID NO:1. The degree of identity between two or more amino acid sequences may be determined by means of computer programs known in the art such as GAP provided in the GCG program package (Needleman and Wunsch, 1970, *Journal of Molecular Biology* 48:443–453).

The amino acid sequences of the homologous glucose oxidases differ from the amino acid sequence set forth in SEQ ID NO:1 by an insertion or deletion of one or more amino acid residues and/or the substitution of one or more amino acid residues by different amino acid residues. The amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine) and small amino acids (such as glycine, alanine, serine, and threonine). Amino acid substitutions which do not generally alter the specific activity are known in the art and are described, e.g., by H. Neurath and R. L. Hill, 1979, in *The Proteins*, Academic Press, New York. The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

The present invention also relates to polypeptides having immunochemical identity or partial immunochemical identity those of a polypeptide native to *Cladosporium oxysporum*. In this embodiment, said polypeptide having glucose oxidase activity is used to produce antibodies which are immunoreactive or bind to epitopes of the polypeptide. A polypeptide having immunochemical identity to the polypeptide native to *Cladosporium oxysporum* means that an antiserum containing antibodies against the polypeptide native to *Cladosporium oxysporum* reacts with the other polypeptide in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis,* Blackwell Scientific Publications, 1973, Chapter 10. Partial immunochemical identity means that an antiserum containing antibodies against the polypeptide native to *Cladosporium oxysporum* reacts with the other polypeptide in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis,* Blackwell Scientific Publications, 1973, Chapter 11. The immunochemical properties are determined by immunological cross-reaction identity tests by the well-known Ouchterlony double immunodiffusion procedure. Specifically, an antiserum against the polypeptide of the invention is raised by immunizing rabbits (or other rodents) according to the procedure described by Harboe and Ingild, In N. H. Axelsen, J. Krøll, and B. Weeks, editors, *A Manual of Quantitative Immunoelectrophoresis,* Blackwell Scientific Publications, 1973, Chapter 23, or Johnstone and Thorpe, *Immunochemistry in Practice,* Blackwell Scientific Publications, 1982 (more specifically pages 27–31).

Preferably, the antibodies are monoclonal antibodies. Monoclonal antibodies may be prepared, e.g., according to the methods of E. Harlow and D. Lane, editors, 1988, *Antibodies, A Laboratory Manual,* Cold Spring Harbor Press, Cold Spring Harbor, N.Y. Purified immunoglobulins may be obtained from the antiserum, e.g., by ammonium sulfate precipitation, followed by dialysis and ion exchange chromatography (e.g., DEAE-Sephadex).

5.2.2. Nucleic Acid Sequences

The present invention also relates to isolated nucleic acid fragments comprising nucleic acid sequences which encode polypeptides having glucose oxidase of the present invention. In a preferred embodiment, the nucleic acid sequence encodes a glucose oxidase obtained from Cladosporium. In a more preferred embodiment the nucleic acid seqeunce is obtained from *Cladosporium oxysporum* and in a most preferred embodiment, the nucleic acid sequence is obtained from Cladosporium, e.g., *Cladosporium oxysporum* CBS 163.94, e.g., the nucleic acid sequence set forth in SEQ ID NO:2. The present invention also encompasses nucleic acid sequences which encode a glucose oxidase having the amino acid sequence set forth in SEQ ID NO:1, which differ from SEQ ID NO:1 by virtue of the degeneracy of the genetic code or a fragment(s) thereof having substantially the same enzyme activity as the full length sequence.

The techniques used to isolate or clone a nucleic acid sequence encoding the glucose oxidase of the present invention are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR). See, e.g., Innis et al., 1990, *A Guide to Methods and Application,* Academic Press, New York. The nucleic acid sequence may be cloned from a strain of the Cladosporium producing the glucose oxidase, or another or related organism and thus, for example, may be an allelic or species variant of the glucose oxidase encoding region of the nucleic acid sequence.

The term "isolated nucleic acid sequence" as used herein refers to a nucleic acid sequence encoding the glucose oxidase of the present invention which is isolated by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the glucose oxidase, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a nucleic acid sequence which has a degree of identity to the nucleic acid sequence set forth in SEQ ID NO. 2 (genomic DNA) or SEQ ID NO. 3 (DNA encompassing coding region) of at least about 50%, preferably about 60%, more preferably about 70%, yet more preferably about 80%, even more preferably about 90%, yet even more preferably about 95%, and most preferably about 97%, which encode an active glucose oxidase. The degree of identity between two nucleic acid sequences may be determined by means of computer programs known in the art such as GAP provided in the GCG program package (Needleman and Wunsch, 1970, *Journal of Molecular Biology* 48:443–453). For purposes of determining the degree of identity between two nucleic acid sequences for the present invention, GAP is used with the following settings: GAP creation penalty of 5.0 and GAP extension penalty of 0.3. The degree of identity between two or more amino acid sequences may be determined by means of computer programs known in the art such as MEGALIGN provided in the DNASTAR program package (Lipman and Pearson, 1985, *Science* 227:1435–1441).

Modification of the nucleic acid sequence encoding the glucose oxidase may be necessary for the synthesis of glucose oxidases substantially similar to the glucose oxidase. The term "substantially similar" to the glucose oxidase refers to non-naturally occurring forms of the glucose oxidase. These glucose oxidases may differ in some engineered way from the glucose oxidase isolated from its native source. For example, it may be of interest to synthesize variants of the glucose oxidase where the variants differ in specific activity, thermostability, pH optimum, or the like using, e.g., site-directed mutagenesis. The analogous sequence may be constructed on the basis of the nucleic acid sequence presented as the glucose oxidase encoding part of SEQ ID NO. 2 or 3, e.g., a sub-sequence thereof, and/or by introduction of nucleotide substitutions which do not give rise to another amino acid sequence of the glucose oxidase encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2:95–107.

It will be apparent to those skilled in the art that such substitutions can be made outside the regions critical to the function of the molecule and still result in an active glucose oxidase. Amino acid residues essential to the activity of the glucose oxidase encoded by the isolated nucleic acid sequence of the invention, and therefore preferably not subject to substitution, may be identified according to procedures known in the art, such as site-directed mutagenesis or alanine-scanning mutagenesis. (see, e.g., Cunningham and Wells, 1989, *Science* 244:1081–1085). In the latter technique mutations are introduced at every residue in the molecule, and the resultant mutant molecules are tested for glucose oxidase activity to identify amino acid residues that are critical to the activity of the molecule. Sites of substrate-enzyme interaction can also be determined by analysis of three-dimensional structure as determined by such techniques as nuclear magnetic resonance analysis, crystallography or photoaffinity labelling (see, e.g., de Vos et al., 1992, *Science* 255, 306–312; Smith et al., 1992, *Journal of Molecular Biology* 224:899–904; Wlodaver et al., 1992, *FEBS Letters* 309, 59–64).

The present invention also relates to nucleic acid sequences which are capable of hybridizing under medium stringency conditions with an oligonucleotide probe which hybridizes under the same conditions with the nucleic acid sequence set forth in SEQ ID NO. 2 or 3 or its complementary strand (Sambrook et al., supra). Hybridization indicates that the analogous nucleic acid sequence hybridizes to the oligonucleotide probe corresponding to the glucose oxidase encoding part of the nucleic acid sequence shown in SEQ ID NO. 2 or 3, specifically, nucleotides 351–2289 of SEQ ID NO. 2 under medium stringency conditions (e.g., prehybridization and hybridization at 42° C. in 5× SSPE, 0.3% SDS, 200 ug/ml sheared and denatured salmon sperm DNA and 35% formamide) following standard Southern blotting.

SEQ ID NO. 2 or 3 may be used to identify and clone DNA encoding polypeptides having glucose oxidase activity from other strains of different genera or species according to methods well known in the art. Thus, genomic, cDNA or combinatorial chemical library prepared from such other organisms may be screened for DNA which hybridizes with SEQ ID NO:2 or 3 and encodes glucose oxidase. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify clones or DNA which is homologous with SEQ ID NO:2 or 3, the carrier material is used in a Southern blot in which the carrier material is finally washed three times for 30 minutes each using 2×SSC, 0.2% SDS at preferably not higher than 50° C., more preferably not higher than 55° C., more preferably not higher than 60° C., more preferably not higher than 65° C., even more preferably not higher than 70° C., especially not higher than 75° C. Molecules to which the oligonucleotide probe hybridizes under these conditions are detected using a X-ray film.

The amino acid sequence set forth in SEQ ID NO:1 may be used to design an oligonucleotide probe, or a gene encoding a glucose oxidase of the present invention or a subsequence thereof can also be used as a probe, to isolate homologous genes of any genus or species. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes, can also be used. Both DNA and RNA probes can be used. The probes are typically labeled for detecting the corresponding gene (for example, with $^{32}P$, $^{3}H$, $^{35}S$, biotin, or avidin). A PCR reaction using the degenerate probes mentioned herein and genomic DNA or first-strand cDNA from a *Cladosporium oxysporum* can also yield a *Cladosporium oxysporum* glucose oxidase-specific product which can then be used as a probe to clone the corresponding genomic or cDNA.

5.2.3. Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into mRNA and translated into a glucose oxidase of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding a polypeptide having glucose oxidase activity may be manipulated in a variety of ways to provide for expression of the polypeptide. Manipulation of the nucleic acid sequence encoding said polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the glucose oxidase. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a glucose oxidase.

The control sequence may be an appropriate promoter sequence, a nucleic acid sequence which is recognized by a host cell for expression of the nucleic acid sequence. The promoter sequence contains transcription and translation control sequences which mediate the expression of the glucose oxidase. The promoter may be any nucleic acid sequence which shows transcriptional activity in the host cell of choice and may be obtained from genes encoding extracellular or intracellular glucose oxidases either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces licheniformis coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Komaroff et al., 1978, Proceedings of the National Academy of Sciences USA 75:3727–3731), as well as the tac promoter (DeBoer et al., 1983, Proceedings of the National Academy of Sciences USA 80:21–25). Further promoters are described in "Useful proteins from recombinant bacteria" in Scientific American, 1980, 242:74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral α-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the glucose oxidase. The terminator sequence may be native to the nucleic acid sequence encoding the glucose oxidase or may be obtained from foreign sources. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of a mRNA which is important for translation by the host cell. The leader sequence is operably linked to the 5' terminus of the nucleic acid sequence encoding the glucose oxidase. The leader sequence may be native to the nucleic acid sequence encoding the glucose oxidase or may be obtained from foreign sources. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. The polyadenylation sequence may be native to the nucleic acid sequence encoding the glucose oxidase or may be obtained from foreign sources. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, Aspergillus nidulans anthranilate synthase, and Aspergillus niger alpha-glucosidase.

Useful polyadenylation sequences for yeast host cells are described by Guo and Sherman, 1995, Molecular Cellular Biology 15:5983–5990. Polyadenylation sequences are well known in the art for mammalian host cells.

The control sequence may also be a signal peptide coding region, which codes for an amino acid sequence linked to the amino terminus of the glucose oxidase which can direct the expressed glucose oxidase into the cell's secretory pathway. The signal peptide coding region may be native to the glucose oxidase of the invention or may be obtained from foreign sources. The 5' end of the coding sequence of the nucleic acid sequence may inherently contain a signal peptide coding region naturally linked in translation reading frame with the segment of the coding region which encodes the secreted glucose oxidase. Alternatively, the 5' end of the coding sequence may contain a signal peptide coding region which is foreign to that portion of the coding sequence which encodes the secreted glucose oxidase. The foreign signal peptide coding region may be required where the coding sequence does not normally contain a signal peptide coding region. Alternatively, the foreign signal peptide coding region may simply replace the natural signal peptide coding region in order to obtain enhanced secretion of the glucose oxidase relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the α-factor from Saccharomyces cerevisiae, an amylase or a protease gene from a Bacillus species, or the calf preprochymosin gene. However, any signal peptide coding region capable of directing the expressed glucose oxidase into the secretory pathway of a host cell of choice may be used in the present invention.

An effective signal peptide coding region for bacterial host cells is the signal peptide coding region obtained from the maltogenic amylase gene from Bacillus NCIB 11837, the Bacillus stearothermophilus alpha-amylase gene, the Bacillus licheniformis subtilisin gene, the Bacillus licheniformis beta-lactamase gene, the Bacillus stearothermophilus neutral proteases genes (nprT, nprS, nprM), and the Bacillus subtilis PrsA gene. Further signal peptides are described by Simonen and Palva, 1993, Microbiological Reviews 57:109–137.

An effective signal peptide coding region for filamentous fungal host cells is the signal peptide coding region obtained from Aspergillus oryzae TAKA amylase gene, Aspergillus niger neutral amylase gene, the Rhizomucor miehei aspartic proteinase gene, the Humicola lanuginosa cellulase gene, or the Rhizomucor miehei lipase gene.

Useful signal peptides for yeast host cells are obtained from the genes for Saccharomyces cerevisiae α-factor and Saccharomyces cerevisiae invertase. Other useful signal peptide coding regions are described by Romanos et al., 1992, supra.

The control sequence may also be a propeptide coding region, which codes for an amino acid sequence positioned at the amino terminus of a glucose oxidase. The resultant glucose oxidase is known as a proenzyme or pro glucose oxidase (or a zymogen in some cases). A pro glucose oxidase can be converted to mature active glucose oxidase by catalytic or autocatalytic cleavage of the propeptide from the pro glucose oxidase. The propeptide coding region may be native to the nucleic acid sequence encoding the glucose oxidase or may be obtained from foreign sources. The propeptide coding region may be obtained from the Bacillus subtilis alkaline protease gene (aprE), the Bacillus subtilis neutral protease gene (nprT), the Saccharomyces cerevisiae alpha-factor gene, or the Myceliophthora thermophilum laccase gene (WO 95/33836).

The nucleic acid constructs of the present invention may also comprise one or more nucleic acid sequences which encode one or more factors that are advantageous in the expression of the glucose oxidase, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the glucose oxidase.

An activator is a protein which activates transcription of a nucleic acid sequence encoding a glucose oxidase (Kudla et al., 1990, EMBO Journal 9:1355–1364; Jarai and Buxton, 1994, Current Genetics 26:2238–244; Verdier, 1990, Yeast 6:271–297). The nucleic acid sequence encoding an activator may be obtained from the genes encoding Bacillus stearothermophilus NprA (nprA), Saccharomyces cerevisiae heme activator protein 1 (hapl), Saccharomyces cerevisiae galactose metabolizing protein 4 (gal4), and Aspergillus nidulans ammonia regulation protein (areA). For further examples, see Verdier, 1990, supra and MacKenzie et al., 1993, Journal of General Microbiology 139:2295–2307.

A chaperone is a protein which assists other proteins in folding to form an active polypeptide (Hartl et al., 1994, TIBS 19:20–25; Bergeron et al., 1994, TIBS 19:124–128; Demolder et al., 1994, Journal of Biotechnology 32:179–189; Craig, 1993, Science 260:1902–1903; Gething and Sambrook, 1992, Nature 355:33–45; Puig and Gilbert, 1994, Journal of Biological Chemistry 269:7764–7771; Wang and Tsou, 1993, The FASEB Journal 7:1515–11157; Robinson: et al., 1994, Bio/Technology 1:381–384). The nucleic acid sequence encoding a chaperone may be obtained from the genes encoding Bacillus subtilis GroE proteins, Aspergillus oryzae protein disulphide isomerase, Saccharomyces cerevisiae calnexin, Saccharomyces cerevisiae BiP/GRP78, and Saccharomyces cerevisiae Hsp70. For further examples, see Gething and Sambrook, 1992, supra, and Hartl et al., 1994, supra.

A processing protease is a protease that cleaves a propeptide: to generate a mature biochemically active glucose oxidase (Enderlin and Ogrydziak, 1994, Yeast 10:67–79; Fuller et al., 1989, Proceedings of the National Academy of Sciences USA 86:1434–1438; Julius et al., 1984, Cell 37:1075–1089; Julius et al., 1983, Cell 32:839–852). The nucleic acid sequence encoding a processing protease may be obtained, for example, from the genes encoding Saccharomyces cerevisiae dipeptidylaminopeptidase, Saccharomyces cerevisiae Kex2, and Yarrowia lipolytica dibasic processing endoprotease (xpr6).

It may also be desirable to add regulatory sequences which allow the regulation of the expression of the glucose oxidase relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, Aspergillus niger glucoamylase promoter, and the Aspergillus oryzae glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the glucose oxidase would be placed in tandem with the regulatory sequence.

5.2.4. Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the glucose oxidase at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis,* or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5′-phosphate decarboxylase), sC (sulfate adenyltransferase), trpC (anthranilate synthase), and glufosinate resistance markers, as well as equivalents from other species.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the glucose oxidase or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence encoding a glucose oxidase of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

5.2.5. Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. The transformation of a bacterial host cell may, for instance, be effected by protoplast transformation (see, e.g., Chang and Cohen, 1979, *Molecular General Genetics* 168:111–115), by using competent cells (see, e.g., Young and Spizizin, 1961, *Journal of Bacteriology* 81:823–829, or Dubnar and Davidoff-Abelson, 1971, *Journal of Molecular Biology* 56:209–221), by electroporation (see, e.g., Shigekawa and Dower, 1988, *Biotechniques* 6:742–751), or by conjugation (see, e.g., Koehler and Thorne, 1987, *Journal of Bacteriology* 169:5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, eg., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a preferred embodiment, the fungal host cell is a yeast cell "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae; (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast,* Bacil, M., Horecker, B. J., and Stopani, A. O. M., editors, 2nd edition, 1987; *The Yeasts,* Rose, A. H., and Harrison, J. S., editors, 2nd edition, 1987; and *The Molecular Biology of the Yeast Saccharomyces,* Strathern et al., editors, 1981).

In a more preferred embodiment, the yeast host cell is a cell of a species of Candida, Kluyveromyces, Saccharomyces, Schizosaccharomyces, Pichia, or Yarrowia. In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma or a teleomorph or synonym thereof. In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell. In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a Fusarium cell of the section Discolor (also known as the section Fusarium). For example, the filamentous fungal parent cell may be a *Fusarium bactridioides, Fusarium cerealis, Fusarium crookwellense, Fusarium culmorum, Fusarium graminearum, Fusarium graminum, Fusarium heterosporum, Fusarium negundi, Fusarium reticulatum, Fusarium roseum, Fusarium sambucinum, Fusarium sarcochroum, Fusarium sulphureum,* or *Fusarium trichothecioides* cell. In another preferred embodiment, the filamentous fungal parent cell is a Fusarium strain of the section Elegans, e.g., *Fusarium oxysporum.* In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78:147–156 or in copending U.S. Ser. No. 08/269,449. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920. Mammalian cells may be transformed by direct uptake using the calcium phosphate precipitation method of Graham and Van der Eb (1978, *Virology* 52:546).

5.3. Industrial Applications

The glucose oxidase of the invention possesses valuable properties allowing for various industrial applications. In particular the enzyme, in having activity in the alkaline region, finds potential application in washing detergent compositions as a hydrogen peroxide source, used alone or preferably together with a peroxidase, more preferably used together with a peroxidase and an oxidizable substrate such as an organic compound, such as a phenolic compound, e.g., p-hydroxybenzenesulfonate, or one of the compounds disclosed in WO 94/12621.

The enzyme may also be very useful in the baking industry due to its excellent ability for improving the properties of doughs/breads).

The enzyme also has many potential applications in the personal care area, for example in personal care products such as tooth paste, mouthwash, denture cleaner, liquid soap, skin care creams and lotions, hair care and body care formulations, and solutions for cleaning contact lenses. In particular, the glucose oxidase of the invention may be very useful in tooth paste, alone or together with other enzymes, preferably together with an amyloglucosidase and a lactoperoxidase as such a combination of enzymes forms a very efficient antibacterial system:

Polysaccharides from plaques→(Amyloglucosidase)
Glucose→(Glucose oxidase of the invention)
Gluconic acid+$H_2O_2$;

the formed hydrogen peroxide may react with thiocyanate in the following way:

$H_2O_2$+SCN→(Lactoperoxidase)
OSCN-, in which OSCN- is a bacteriostatic agent 5.3.1. Gluten Strengthening It is generally known that dough stability is one of the most important characteristics of a baking dough. Stable dough is important for both large scale and small scale applications. A strong dough will exhibit a greater tolerance of mixing time, of proofing time and of mechanical vibrations during dough transport, so that the baked product maintains its good quality. A weak dough will possess less tolerance. Therefore, a strong dough is generally preferred in most breadmaking. A high gluten content and a good gluten quality form a stronger dough than a dough made from a low protein content or with poor gluten quality. In other words, a strong gluten network results in a strong dough, which has superior Theological and handling properties.

Dough "conditioners" to strengthen the gluten have long been used. The non-specific oxidants, such as bromate, ascorbic acid and peroxides have the gluten strengthening effect. It has been suggested that these conditioners induce the interprotein bonds which strengthen the gluten, thereby the dough. Enzymes used as dough conditioners are also known, e.g. glucose oxidase from *Aspergillus niger.*

The strengthening effect of a given dough conditioner on wheat flour dough or gluten dough may be measured by dynamic Theological measurements. These measurements are able to show the strength of a dough, under oscillation. Both wheat fluor dough and gluten dough are viscoelastic materials. In oscillatory measurements, the viscoelastic properties of a wheat dough and a gluten dough can be divided into two components, the dynamic shear storage modulus G' and the dynamic shear loss modulus G". The ratio of the loss and the storage moduli is numerically equal to the tangent of the viscoelastic phase angle λ. An increase in the storage modulus G' and a decrease in the phase angle λ indicate a stronger and more elastic dough.

5.3.2. Baking industry/Additional Enzyme Activities

While the bread-improving composition or additive may comprise a glucose oxidase as the only enzyme added, the properties of dough and/or baked products may be further improved when the glucose oxidase is used in combination with one or more additional enzymes.

The additional enzyme(s) may either be one or more enzymes present in the glucose oxidase preparation recovered from the organism producing it, or may, more preferably, be added to the bread-improving composition or additive.

In a preferred embodiment, the additional enzyme is selected from the group consisting of an amylase, in particular an amyloglucosidase, an α-amylase or a maltogenic exo-amylase (at present contemplated useful for providing sugars fermentable by yeast), a peptidase, a maltogenase, a lipase, a cellulase, a hemicellulase, in particular a xylanase, a protease (at present contemplated useful for gluten weakening in particular when using hard wheat flour), and an oxidoreductase, e.g., a peroxidase, a laccase, a protein disulfide isomerase, e.g., a protein disulfide isomerase as disclosed in WO 95/00636, or an additional glucose oxidase.

In a more preferred embodiment, the additional enzyme is selected from the group consisting of a hemicellulase, in particular a xylanase, and an amylase, e.g., an amyloglucosidase, an a-amylase or a maltogenic exo-amylase.

The additional enzyme is preferably of microbial (bacterial, yeast or fungal) origin and may be obtained by techniques conventionally used in the art.

The amylase may be derived from a bacterium or a fungus, in particular from a strain of Aspergillus, preferably a strain of *Aspergillus niger* or *Aspergillus oryzae*, or from a strain of Bacillus. Commercially available α-amylases useful for the present purpose are Fungamyl™ (an *Aspergillus oryzae* α-amylase, available from Novo Nordisk A/S, Denmark), Novamyl™ (a *Bacillus stearothermophilus* maltogenic exo-amylase, available from Novo Nordisk A/S, Denmark), and BAN™ (a *Bacillus amyloliquefaciens* α-amylase, available from Novo Nordisk A/S, Denmark). The amyloglucosidase may in particular be AMG™ (an *A. niger* amyloglucosidase, available from Novo Nordisk A/S, Denmark). Other useful amylase products include Grindamyl™ A 1000 or A 5000 (available from Grindsted Products, Denmark) and Amylase™H or Amylase™P (available from Gist-Brocades, The Netherlands).

The additional glucose oxidase may be a fungal glucose oxidase, in particular Gluzyme™ (an *Aspergillus niger* glucose oxidase, available from Novo Nordisk A/S, Denmark).

The lipase may be derived from a strain of Thermomyces, a strain of Rhizomucor, a strain of Candida, a strain of Aspergillus, a strain of Rhizopus, or a strain of Pseudomonas. In particular the lipase may be derived from a strain of *Thermomyces lanuginosus,* a strain of *Rhizomucor miehei,* a strain of *Candida antarctica,* a strain of *Aspergillus niger,* or a strain of *Pseudomonas cepacia.* In specific embodiments, the lipase may be Lipase A or Lipase B derived from a strain of *Candida antarctica* as described in WO 88/02775, or the lipase may be derived from a strain of *Rhizomucor miehei* as described in EP 238,023, or a strain of *Humicola lanuginosa* described in EP 305,216, or a strain of *Pseudomonas cepacia* as described in EP 214,761 and WO 89/01032.

Besides the above mentioned additional enzymes, a microbial produced glucose oxidase preparation may contain varying minor amounts of other enzymatic activities inherently produced by the producer organism in question.

5.3.3. Detergent Compositions

According to the invention, the glucose oxidase may typically be a component (a hydrogen peroxide source) of a detergent composition, e.g., a laundry detergent composition or a dishwashing detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may for instance, be stabilized by adding a polyol such as propylene glycol, a sugar or sugar alcohol, lactic acid or boric acid according to established methods. Other enzyme stabilizers are well known in the art.

Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or amphoteric (zwitterionic). The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as pullulanase, esterase, lipase, cutinase, protease, cellulase, or peroxidase.

Normally the detergent contains 1–65% of a detergent builder, but some dishwashing detergents may contain even up to 90% of a detergent builder, or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorus-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates. The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, polymaleates, maleic/acrylic acid copolymers and lauryl methacrylate/acrylic acid copolymers.

The detergent composition may additionally contain other bleaching agents of the chlorine/bromine-type or the oxygen-type. The bleaching agents may be coated or encapsulated. Examples of inorganic chlorine/bromine-type bleaches are lithium, sodium or calcium hypochlorite or hypobromite as well as chlorinated trisodium phosphate.

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium.

Hydantoin compounds are also suitable. The bleaching system may also comprise peroxyacids of, e.g., the amide, imide, or sulfone type.

In dishwashing detergents, the oxygen bleaches are preferred, for example, in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED or NOBS.

The enzymes of the detergent composition of the invention may be stabilized using conventional stabilizing agents, e.g., a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type as described in EP 0 544 777 B1.

The detergent may also contain other conventional detergent ingredients such as, e.g., fabric conditioners including clays, deflocculant material, foam boosters/foam depressors (in dishwashing detergents foam depressors), suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g., in the range of 7–11.

The glucose oxidase of the invention may be incorporated in concentrations conventionally employed in detergents. It is at present contemplated that, in the detergent composition of the invention, the glucose oxidase may be added in an amount corresponding to 0.00001–1 mg (calculated as pure enzyme protein) of glucose oxidase per liter of wash/dishwash liquor.

The present invention is further illustrated in the following examples which are not intended to be in any way limiting to the scope of the invention as claimed.

6. EXAMPLES 6.1. Purification of the Glucose, oxidase from Cladosporium 6.1.1. Glucose oxidase purification assay Glucose oxidase oxidizes β-D-glucose to D-gluconic acid and hydrogen peroxide in the presence of oxygen. The formed hydrogen peroxide can be used by peroxidase to oxidize ABTS to a coloured product, which can be monitored at $OD_{405}$. The above principle is used to make a coupled enzyme assay, where the increase in $OD_{405}$ is a measure of the glucose oxidase activity.

The following reagents are made fresh: 1) Assay buffer: 0.10M Na-acetate/HCl, pH 5.6, 2) Peroxidase(POD) solution: 2 mg Peroxidase (Sigma, P-8125) is dissolved in 4.0 ml assay buffer, 3) Glucose solution: 1.8 g D-Glucose is dissolved in assay buffer and assay buffer is added ad 10.0 ml, and 4) ABTS solution: 2.5 mg ABTS (2,2'-Azinobis(3-ethylbenzthiazoline-6-sulfonic acid), Sigma A-1888) is dissolved in assay buffer and assay buffer is added at 10.0 ml. The ABTS reagent is kept dark.

Before use, a Glucose-POD-ABTS solution is made by mixing 100 µl POD solution, 900 µl Glucose solution, and 9000 µl ABTS solution. After preparing the solution, the solution is left for at least 30 minutes to ensure mutarotation, but kept dark.

20 µl samples of the glucose oxidase fractions in question (diluted in assay buffer) are pipetted into microtiter plate wells. The enzyme reaction is started by adding 200 µl Glucose-POD-ABTS-reagent solution to each well. The increase in $OD_{405}$ is monitored by the absorbance at 405 nm and corresponds to the glucose oxidase activity.

6.1.2. Starting material

OBF1003, UFkonc.3, BMN, 111194 is a concentrated (ultrafiltrated) filtrate of a *Cladosporium oxysporum* broth.

6.1.3. Purification

Solid ammonium sulphate is added to 2.0 L starting material to give a final ammonium sulphate concentration of 3.0M. Material precipitated by the ammonium sulphate is removed by filtration.

The filtrate is applied to a 500 ml Phenyl-Sepharose FF column equilibrated in 100 mM $H_3BO_3$, 10 mM dimethylglutaric acid, 2 mM $CaCl_2$, 3.0M $(NH_4)_2SO_4$, pH 7.0. After washing the column with the equilibration buffer, bound protein is eluted with a linear $(NH_4)_2SO_4$ gradient (3.0→0M) over 2 column volumes. Glucose oxidase containing fractions are pooled.

The buffer of the Phenyl-Sepharose pool is exchanged with 20 mM Tris/$CH_3COOH$, pH 7.5, by a pass on a Sephadex G25 column. The enzyme is applied to a 100 ml Q-Sepharose FF column equilibrated in 20 mM Tris/$CH_3COOH$, pH 7.5. After washing the column with equilibration buffer, the glucose oxidase activity is eluted with a linear NaCl gradient (0→1.0M) over 5 column volumes. Glucose oxidase containing fractions are pooled.

The Q-Sepharose pool is dialysed against distilled water for two hours and applied to a 22 ml SOURCE Q (Pharmacia, anion exchange) column equilibrated in 20 mM Tris/$CH_3COOH$, pH 7.5. After washing the column with the equilibration buffer, the glucose oxidase activity is eluted with a linear NaCl gradient (0→1.0M) over 30 column volumes. Glucose oxidase containing fractions are pooled and diluted 5 times with distilled water and applied again to the same SOURCE Q column equilibrated in 20 mM Tris/$CH_3COOH$, pH 7.5. After washing the column with the equilibration buffer, the glucose oxidase activity is eluted with a linear NaCl gradient (0→0.2M) over 30 column volumes. Glucose oxidase containing fractions are pooled.

Solid ammonium sulphate is added to the second SOURCE Q pool to give a final ammonium sulphate concentration of 3.0M. The glucose oxidase is applied to an 8 ml SOURCE Phenyl column equilibrated in 100 mM $H_3BO_3$, 10 mM dimethylglutaric acid, 2 mM $CaCl_2$, 3.0M $(NH_4)_2SO_4$, pH 7.0. After washing the column thoroughly with the equilibration buffer, the glucose oxidase activity is eluted with a linear $(NH_4)_2SO_4$ gradient (3.0→0M) over 40 column volumes. The glucose oxidase activity did not elute in a single sharp peak, but rather in a multitude of (sharp) peaks. When these glucose oxidase peaks are analysed by SDS-PAGE it is seen that the multitude of glucose oxidase peaks most likely represent a heterogeneous glycosylation pattern for the glucose oxidase enzyme. Glucose oxidase containing fractions are pooled.

The SOURCE Phenyl pool is concentrated using an Amicon ultrafiltration cell (with a cut-off=2 kDa membrane) to 2.0 ml and applied to a 100 ml Sephacryl S-100 column equilibrated in 20 mM $CH_3COOH$/NaOH, 100 mM NaCl, pH 6.0. Fractions eluted from the column are analysed by SDS-PAGE. Fractions with one (broad glycosylated) band are pooled as the Cladosporium glucose oxidase.

6.2 Amino acid sequences from *Cladosporium oxysporum* glucose oxidase

The N-terminal amino acid sequence of purified *Cladosporium oxysporum* glucose oxidase is determined directly and following electroblotting using an Applied Biosystems 473A protein sequencer. The enzyme has a molecular weight above 100 kDa and appears as a broad band on SDS-PAGE indicating significant glycosylation. Direct sequencing and sequencing following electroblotting gives the same N-terminal amino acid sequence:

Ala-Glu-Ser-Ala-His-Ala-Ile-Thr-Ala-Asp-Val-Ser-Gln-Val- (SEQ ID NO:4)

The *Cladosporum oxysporum* glucose oxidase is reduced and S-carboxymethylated before degradation with either a lysyl-specific protease or the Asp-N protease. The resulting peptides are fractionated and repurified using reverse-phase HPLC before being subjected to N-terminal amino acid sequenceing. The following ten peptide sequences are obtained. Peptides B,C, and F are obtained following Asp-N degradation.

N-terminal (residues 1–14):

Ala-Glu-Ser-Ala-His-Ala-Ile-Thr-Ala-Asp-Val-Ser-Gln-Val- (SEQ ID NO:15)

Peptide C (residues 62–71):

Asp-Val-Arg-Thr-Tyr-Gly-Gln-Ala-Phe-Glu- (SEQ ID NO:16)

Peptide G (residues 80–97):

Ser-Thr-Ser-Val-Pro-Trp-Gln-Xaa-Asn-Thr-Gly-Leu-Leu-Leu-Val-Ala-Gly-Lys (SEQ ID NO:17)

Xaa is most probably a glycosylated Asn-residue as the consensus sequence for N-glycosylation is found. In addition, Asn is found at this position in the DNA sequence.

Peptide 2 (residues 116–144):

Thr-Gln-Tyr-Asp-Leu-Leu-Pro-Gly-Leu-Thr-Gly-Asp-Asp-Ser-Trp-Ser-Phe-Asp-Ala-Leu-Asn-Glu-Ile-Met-Leu-Ser-Ile-Glu-Asp- (SEQ ID NO:6)

Peptide D (Residues 200–228):

Val-Ala-Asp-Phe-Ala-Ala-Gly-Ile-Thr-Thr-Gly-Ala-Thr-Met-Ile-Pro-Asn-Met-Leu-Glu-Ala-Asn-Glu-Ser-Gln-Xaa-Arg-Ser-Ser- (SEQ ID NO:18)

Xaa is most probably a glycosylated Asn-residue as the consensus sequence for N-glycosylation is found. In addition, Asn is found at this position in the DNA sequence.

Peptide F (residues 286–296):

Glu-Val-Leu-Leu-Ala-Gly-Gly-Ser-Leu-Gln-Ser- (SEQ ID NO:19)

Peptide E (residues 335–370):

Asn-Thr-Leu-Trp-Phe-Asp-Pro-Val-Asn-Thr-Glu-Phe-Asp-Gly-Ser-Gly-Pro-Pro-Asn-Ala-Ile-Ser-Phe-Pro-Asn-Val-Asp-Gln-Leu-Phe-Arg-Xaa-Asn-Yaa-Ala-Thr- (SEQ ID NO:20)

Xaa is most probably a glycosylated Asn-residue. In addition, Asn is found at this position in the DNA sequence. Yaa is a residue that could not be assigned. Ser is found at this position in the DNA sequence, meaning that the consensus sequence for N-glycosylation is present.

Peptide 3 (Residues 381–434):

Gln-Tyr-Ser-Glu-Asp-Leu-Ala-Ala-Thr-Gly-Thr-Val-Thr-Xaa-Ala-Thr-Ala-Thr-His-Gln-Ile-Leu-Glu-Ala-Gln-Val-Asp-Asn-Leu-Trp-His-Asn-Leu-Val-Gly- Ala-Ala-Glu-Ile-Phe-Phe-Val-Thr-Ser-Pro-Ala-Thr-Gly-Gln-Val-Gly-Val-Asp-Leu- (SEQ ID NO:7)

Peptide B (residues 454–467):

Asp-His-Pro-Glu-Ile-Glu-Pro-Ser-Tyr-Phe-Gly-His-Gln-Phe (SEQ ID NO:21)

Peptide 1 (residues 518–534):

Ala-Thr-Phe-Thr-Ser-Val-Trp-His-Tyr-Ile-Ala-Thr-Leu-Gly-Met-Met-Lys (SEQ ID NO:5)

Peptide A (residues 547–567):

Val-Tyr-Gly-Ile-Glu-Asn-Val-Xaa-Ala-Val-Asp-Ala-Ser-Val-Leu-Pro-Ile-Gln-Leu-Ser-Ala- (SEQ ID NO:22)

Xaa is a residue that could not be assigned. Arg is found at this position in the DNA sequence.

6.3. Cloning of *Cladosporium oxysporum* Glucose Oxidase 6.3.1.Bacterial Strains and Cloning Vectors Genomic DNA libraries are constructed using the λZipLox cloning system (Life Technologies, Gaithersburg, Md.) with *E. coli* Y1090ZL as a host for plating and purification of recombinant bacteriophage and *E. coli* DH10Bzip for excision of individual pZL1-glucose oxidase clones.

6.3.2.DNA Extraction

Total cellular DNA is extracted from fungal cells grown 24 hours at 32° C. in 25 ml of YEG medium (0.5% yeast extract, 2% glucose) using the following protocol: Mycelia are collected by filtration through Miracloth (Calbiochem, La Jolla, Calif.) and washed once with 25 ml of TE buffer (20 mM Tris-HCl, 1 mM EDTA, pH 8.0). Excess buffer is drained from the mycelia which are subsequently frozen in liquid nitrogen. Frozen mycelia are ground to a fine powder in an electric coffee grinder, and the powder added to 20 ml of TE buffer and 5 ml of 20% SDS (w/v) in a disposable plastic centrifuge tube. The mixture is gently inverted several times to ensure mixing, and extracted twice with an equal volume of phenol:chloroform:isoamyl alcohol (25:24:1, v/v). Sodium acetate (3M solution) is added to give a final concentration of 0.3M and the nucleic acids are precipitated with 2.5 volumes of ice cold ethanol. The tubes are centrifuged at 15,000×g for 30 min and the pellet is allowed to air-dry for 30 min before resuspending in 0.5 ml of TE buffer. DNase-free ribonuclease A is added to a concentration of 100 μg/ml and the mixture is incubated at 37° C. for 30 min. Proteinase K (200 μg/ml) is added and each tube is incubated an additional one hour at 37° C. Finally, each sample is extracted twice with phenol:chloroform:isoamyl alcohol before precipitating the DNA with sodium acetate and ethanol. DNA pellets are dried under vacuum, resuspended in TE buffer, and stored at 4° C.

6.3.3.Hybridization Analysis of Genomic DNA

Total cellular DNA samples from *C. oxysporum* A4591 are analyzed by Southern hybridization (Davis et al., 1980, Advanced Bacterial Genetics, A Manual for Genetic Engineering, ° Cold Spring Harbor Press, Cold Spring Harbor, N.Y.). Approximately 2–5 μg of DNA is digested with various restriction enzymes (Boehringer Mannheim, Indianapolis, Ind.) and fractionated on a 1% agarose gel. The gel is photographed under short wavelength UV light and soaked for 15 minutes in 0.5M NaOH, 1.5M NaCl followed by 15 minutes in 1M Tris-HCl, pH 8, 1.5M NaCl. DNA in the gel is transferred onto Nytran™ hybridization membrane (Schleicher & Schuell, Keene, N.H.) by capillary blotting in 20× SSPE (Davis et al., 1980, Advanced Bacterial Genetics, A Manual for Genetic Engineering. Cold Spring Harbor Press, Cold Spring Harbor, N.Y.). The DNA is cross-linked onto the membrane using a UV Stratalinker (Stratagene, La Jolla, Calif.), and the membrane is soaked for 30 min. in DIG Easy Hyb (Boehringer Mannheim, Indianapolis, Ind.) hybridization buffer at 42° C. with gentle agitation. A glucose oxidase-specific probe fragment is generated by PCR-amplification using primers GOX1 and GOX2 (described below). The probe is purified using QiaQuick Spin purification columns (Qiagen Inc.) and resuspended at a concentration of 50 ng/μl after quantification using DIG Quantification Teststrips (Boehringer Mannheim, Indianapolis, Ind.). The purified probe is diluted to 1 ng/ml in DIG Easy Hyb and denatured by immersion in a boiling water bath for 2 min. and added to the filter. The mixture is incubated overnight at 42° C. in a shaking water bath. Following incubation, the membranes are washed twice in 0.2 ×SSC with 0.1% SDS at room temperature followed by two washes in 0.1×SSC, 0.1% SDS at 68° C. with constant agitation. The membranes are then incubated with anti-DIG antibody conjugated to alkaline phosphatase according to the manufacturer's instructions, and the filters are coated with the chemiluminescent substrate CBD-star (Boehringer Mannheim, Indianapolis, Ind.) prior to exposing them to X-ray film.

6.4. PCR Amplifications

Based on amino acid sequence data from purified *C. oxysporum* glucose oxidase and preliminary sequence data (see below), the following oligonucleotide primers are designed for use in PCR experiments:

forward primers:

| | |
|---|---|
| gox 1F: | dGCNCAYGC5ATHAC5GCNGAYGT (based on N-terminal peptide) (SEQ ID NO:8) |
| GOX1: | dGAGGACTTACGGACAAGCCTT (SEQ ID NO:9) |
| GOXpcr1: | dCCACCATGTACAAACCCATCGCGC (SEQ ID NO:10) |

Reverse primers:

| | |
|---|---|
| gox4A-R: | dCATDATYTCRTT5AG5GCRTCRAA (based on internal peptide) (SEQ ID NO:11) |
| gox5A-R | dTTRTGCCA5AGRTTRTCNAC (based on internal peptide) (SEQ ID NO:12) |
| GOX2: | dATCAACCTGTGCTTCGAGGAT (SEQ ID NO:13) |
| GOXpcr-2: | dCCCTTAATTAACGCTCATCACGCCCTCTGATCCTC (SEQ ID NO:14) | where D=A, G or T, Y=C or T, R=A or G, N=A, C, G, or T, and 5=I.

Amplification reactions (100 μl) are prepared using approximately 1 μg of *C. oxysporum* genomic DNA as the template. In addition, each reaction contains the following components: 40 pmol forward primer, 40 pmol reverse primer, 200 μM each of dATP, dCTP, dTTP, and dGTP, 1×Taq polymerase buffer (Perkin-Elmer Corp., Branchburg, N.J.), and 5 units of Taq polymerase (Perlin-Elmer). Sterile mineral oil (100 μl) is layered on top of each reaction mixture, and the reactions are incubated in a Perkin-Elmer Model 480 Thermal Cycler programmed as follows: Cycle 1; 95° C. for 5 min, 45° C. for 2 min, 67° C. for 5 min. Cycle 2-30; 95° C. for 2 min; 45° C. for 2 min, 67° C. for 2 min. Soak cycle; 4° C. The reaction products are isolated on a 1% low melting point agarose gel (Sigma Chemical Co., St. Louis, Mo.). Bands are excised from the gel and purified using β-agarase (New England Biolabs, Beverly, Mass.) according to the manufacturer's instructions. The purified PCR products are subsequently cloned into a pCRII vector (Invitrogen, San Diego, Calif.) and analyzed by DNA sequencing.

Amplification reactions for DIG probe construction are performed using 1 μl of the 1200 bp PCR product from a PCR reaction using primers gox1F and gox5A-R as template in a reaction containing 40 pmol primer GOX1, 40 pmol primer GOX2, 200 μM each of dATP, dCTP, dTTP, and dGTP with DIG-labeled dCTP, 1×Taq polymerase buffer (Perkin-Elmer Corp., Branchburg, N.J.), and 2.5 units of Taq polymerase (Perkin-Elmer) in a 50 μl reaction volume.

Various combinations of primers are tested and two combinations resulted in prominent bands of 400 bp (primers gox1F and gox4A-R) and 1200 bp (primers gox1F and gox5A-R). Both products are cloned into the pCRII vector (Invitrogen, San Diego, Calif.) and sequenced. The nucleotide sequence of the cloned 400 bp fragment revealed that it is a 5' subsequence of the 1200 bp cloned fragment, since both products are amplified using the same 5' primer (gox1F). The DNA sequence data from the 1200 bp clone is then used to design GOX-specific PCR primers (GOX1 and GOX2) for use in the generation of a DIG-labeled probe fragment approximately 1 kb in length.

The gox1 gene used in construction of expression plasmid pGOX3.3 is amplified by PCR using a sense primer (GOXpcr1, see above) designed to add the sequence CCACC just upstream of the initiator ATG. The antisense primer (GOXpcr-2) contains the transcriptional stop and terminates at its 5' end with a PacI restriction site to facilitate the cloning of the amplified fragment. The 50 μl PCR reaction contained 1× Pwo Polymerase Buffer (Boehringer Mannheim, Indianapolis, Ind.), 200 μM each dNTP, approximately 200 ng of *C. oxysporum* genomic DNA, and 50 pmol of each PCR primer. Five units of Pwo polymerase (Boehringer Mannheim, Indianapolis, Ind.)) are added after the reaction incubated at 95° C. for 3 minutes and reaction is then cycled 30 times as follows: 95° C. for 30 seconds, 57° C. for 1 minute, 72° C. for 1 minute. Following the last cycle, the reaction is incubated for an additional 5 minutes at 72° C.

6.5. DNA Libraries and Identification of Glucose Oxidase Clones

Genomic DNA libraries are constructed using the λZipLox cloning system (Life Technologies, Gaithersburg, Md.). Briefly, total cellular DNA is partially digested with Tsp509I and size-fractionated on 1% agarose gels. DNA fragments migrating in the size range 3–7 kb are excised and eluted from the agarose gel slices using Prep-a-Gene reagents (BioRad). The eluted DNA fragments are ligated with EcoRI-cleaved and dephosphorylated λZipLox vector arms (Life Technologies, Inc.), and the ligation mixtures are packaged using commercial packaging extracts (Stratagene, La Jolla, Calif.). The packaged DNA libraries are plated and amplified on *Escherichia coli* Y1090ZL cells. The unamplified genomic library contained $4.9\times10^6$ pfu/ml (a control ligation with no genomic DNA inserts yielded $2\times10^4$ pfu/ml). Approximately 120,000 plaques from the library are screened by plaque-hybridization (Davis et al., 1980, Advanced Bacterial Genetics, A Manual for Genetic Engineering. Cold Spring Harbor Press, Cold Spring Harbor, N.Y.) with a DIG-labeled probe fragment of the *C. oxysporum* glucose oxidase gene using the conditions described above.

Four plaques which hybridize strongly are picked, plaque-purified on *E. coli* Y1090ZL cells, and each of the clones are subsequently excised from the λZipLox vector as pZL1-derivatives. Miniprep DNA is prepared from each of these clones and the sizes of the glucose oxidase inserts are determined by agarose gel electrophoresis. Clones 4A and 7A contained a ~2.5 kb insert while clones 6A and 10B contained a −3.5 kb insert. Southern analysis confirms that all four clones hybidized to the GOX probe. Sequencing reveals that clones 4A and 7A are siblings, as are 6A and 10B (hereafter referred to as clones 4A and 6A, respectively). While the two clones shares no homology to one another, both are homologous to 1 kB GOX1–GOX2 PCR fragment. Clones 4A and 6A are therefore concluded to represent non-overlapping but contiguous 5' and 3' ends of the GOX gene. The 4A and 6A clones contain a Tsp509I site (that is used in the construction of the genomic library) at their 3' and 5' ends, respectively. The assembled 2386 bp sequence contains the *C. oxysporum* glucose oxidase gene gox1 as determined by DNA sequencing.

6.6. Analysis of the *C. oxysporum* Glucose Oxidase Gene

DNA sequencing is performed with an Applied Biosystems Model 373A Automated DNA Sequencer (Applied Biosystems, Inc., Foster City, Calif.) using the primer walking technique with dye-terminator chemistry (Giesecke et al., 1992, J. Virol. Methods 38:47–60). Oligonucleotides are synthesized on an Applied Biosystems model 394 DNA/RNA Synthesizer.

Figure 2A:
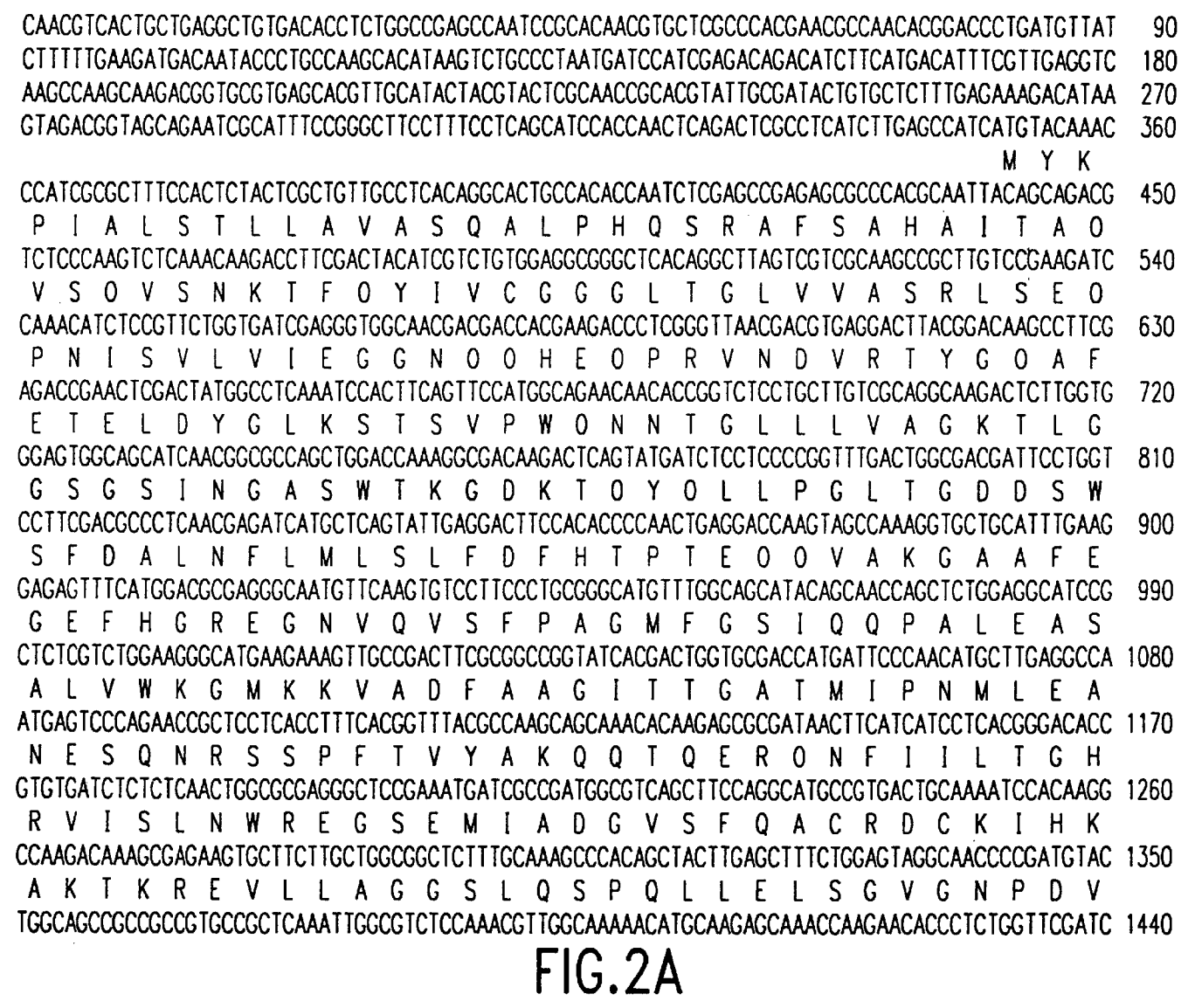

DNA sequence analysis of the cloned gox1 inserts revealed a large open reading frame of 1839 nucleotides (excluding stop codon) encoding a protein of 613 amino acids (FIG. 3). The G+C content of this open reading frame is 56%, while the 350 bp of untranslated upstream sequence is 52% G+C and the 197 bp of untranslated downstream sequence is 58% A+T. The upstream sequences lack a canonical TATA element, but contains a CATAA, as well as two CAAT boxes as indicated in FIG. 2. There are no introns present in the gene. The veracity of the reading frame is supported by the occurrence within the predicted peptide of four sequenced peptides comprising a total of 113 amino acids derived from purified GOX. The N-terminus of the mature protein begins at amino acid 24 of the predicted protein, suggesting a signal sequence/propeptide of 23 amino acids. Using a computer program that analyses signal sequence probability according to the rules of von Heijne (1986, Nucl. Acids Res. 14:4683–4690), the most likely site of signal sequence cleavage occurs between residues 19 and 20 (FIG. 3). This suggests that residues 20 through 23 may constitute a short pro-region that is proteolytically removed during maturation.

The *C. oxysporum* GOX shares only 27% amino acid sequence identity with the only other cloned glucose oxidase, that isolated from *A. niger* (FIG. 3).

6.7. Construction of a Fusarium expression cassette

A Fusarium expression cassette is constructed using the technique of overlapping PCR (see Innis et al., 1990, *PCR Protocols: A Guide to Methods and Applications,* Academic Press, New York, pages 177–183) to fuse the 1.24 kb *Fusarium oxysporum* trypsin gene promoter to the 1.1 kb *Fusarium oxysporum* trypsin gene terminator (Royer et al., 1995, *Bio/Technology* 13: 1479–1483). A polylinker containing SwaI, KpnI, and PacI restriction sites is inserted between the promoter and terminator as part of the overlapping PCR strategy. At the 5' end of the promoter an XhoI site is added and the native EcoRI site is preserved. At the 3' end of the terminator, EcoRI, HindIII and NsiI sites are incorporated by the PCR reaction.

A PCR fragment containing –1208 to –1 of the *Fusarium oxysporum* promoter plus a 25 base pair polylinker is generated from pJRoy20 (Royer et al., 1995, supra) using the following primers:

```
                         XhoI    EcoRI
Primer 1 (sense):    5'-dGAGCTCGAGGAATTCTTACAAACCTTCAAC-3' (SEQ ID NO:23)
                         PacI    KpnI         SwaI
Primer 2 (antisense): 5'-dTTAATTAAGGTACCTGAATTTAAATGGTGAAGAGA
TAGATATCCAAG-3' (SEQ ID NO:24)
```

The 100 μl PCR reaction contained 1×pwo DNA polymerase buffer (Boehringer Mannheim, Indianapolis, Ind.), 200 μM each of dATP, dCTP, dGTP, and dTTP, 10 ng pjRoy20, and 5 units pwo DNA polymerase (Boehringer Mannheim, Indianapolis, Ind.). PCR conditions used are 95° C. for 3 minutes followed by 25 cycles each at 95° C. for 30 seconds, 50° C. for 1 minute, and 72° C. for 1 minute. The final extension cycle is at 72° C. for 5 minutes.

Using the same PCR conditions, a second PCR fragment containing –5 to –1 of the *Fusarium oxysporum* trypsin gene promoter, the 25 base pair polylinker, and 1060 base pairs of the 3' untranslated region of the *Fusarium oxysporum* trypsin gene (terminator region) is generated from plasmid pJRoy20 using the following primers:

```
                         SwaI         KpnI         PacI
Primer 3 (sense):    5'-dTCACCATTTAAATTCAGGTACCTTAATTAAATTCCT
TGTTGGAAGCGTCGA-3' (SEQ ID NO:25)
                         NsiI   HindII   EcoRI
Primer 4 (antisense): 5'-dTGGTATGCATAAGCTTGAATTCAGGTAAAC
AAGATATAATTT-3' (SEQ ID NO:26)
```

The final 2.3 kb overlapping PCR fragment which contains –1208 to –1 of the *Fusarium oxysporum* trypsin gene promoter, the 25 base pair polylinker, and 1060 base pairs of the *Fusarium oxysporum* trypsin gene terminator is made using 0.2 μl of the first PCR (promoter) reaction and 3 μl of the second (terminator) reaction as template and primers 1 and 4. The PCR conditions used are 95° C. for 3 minutes followed by 30 cycles each at 95° C. for 30 seconds, 62° C. for 1 minute, and 72° C. for 3 minutes. The final extension cycle is at 72° C. for 5 minutes. Pwo DNA polymerase is also used for this reaction.

Figure 4:
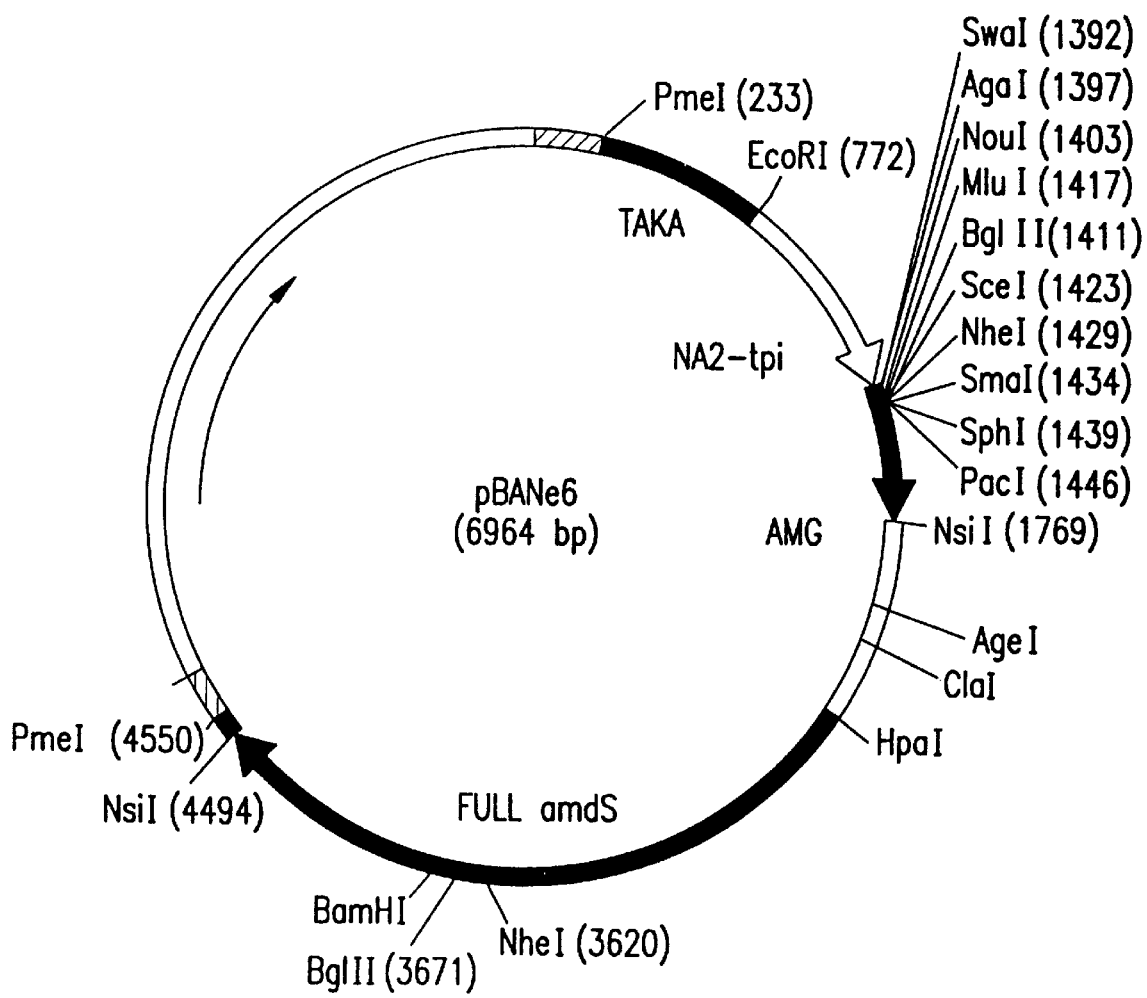
FIG. 4 shows the restriction map of pBANe6.
Figure 5:
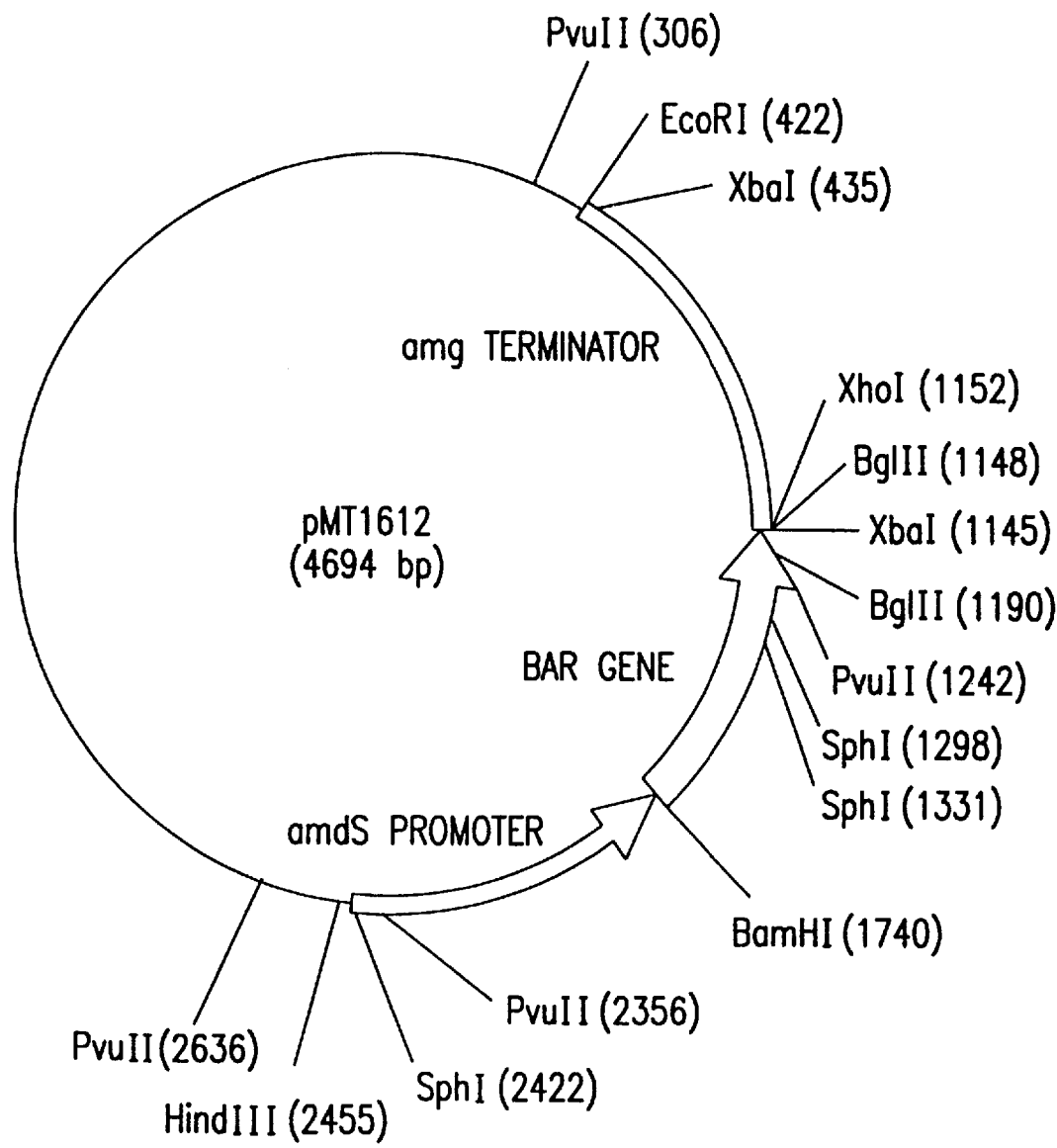
FIG. 5 shows the restriction map of plasmid pMT1612.
Figure 6:
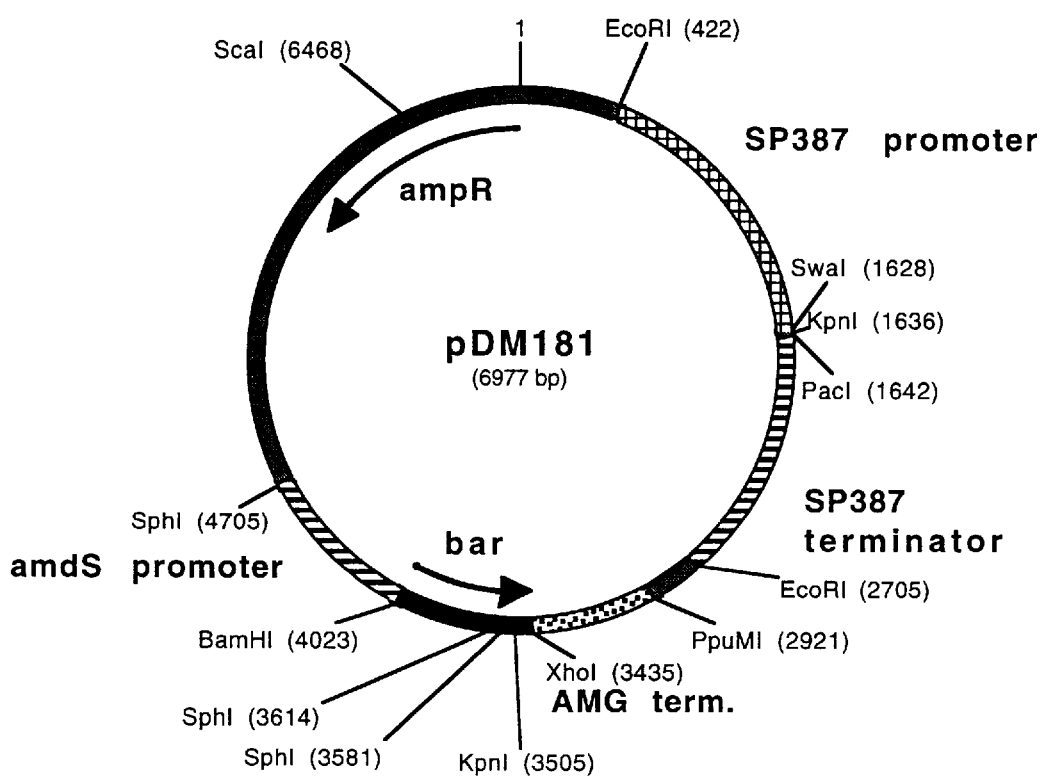
FIG. 6 shows the restriction map of fusarium expression cassette pDM181.
Figure 7:
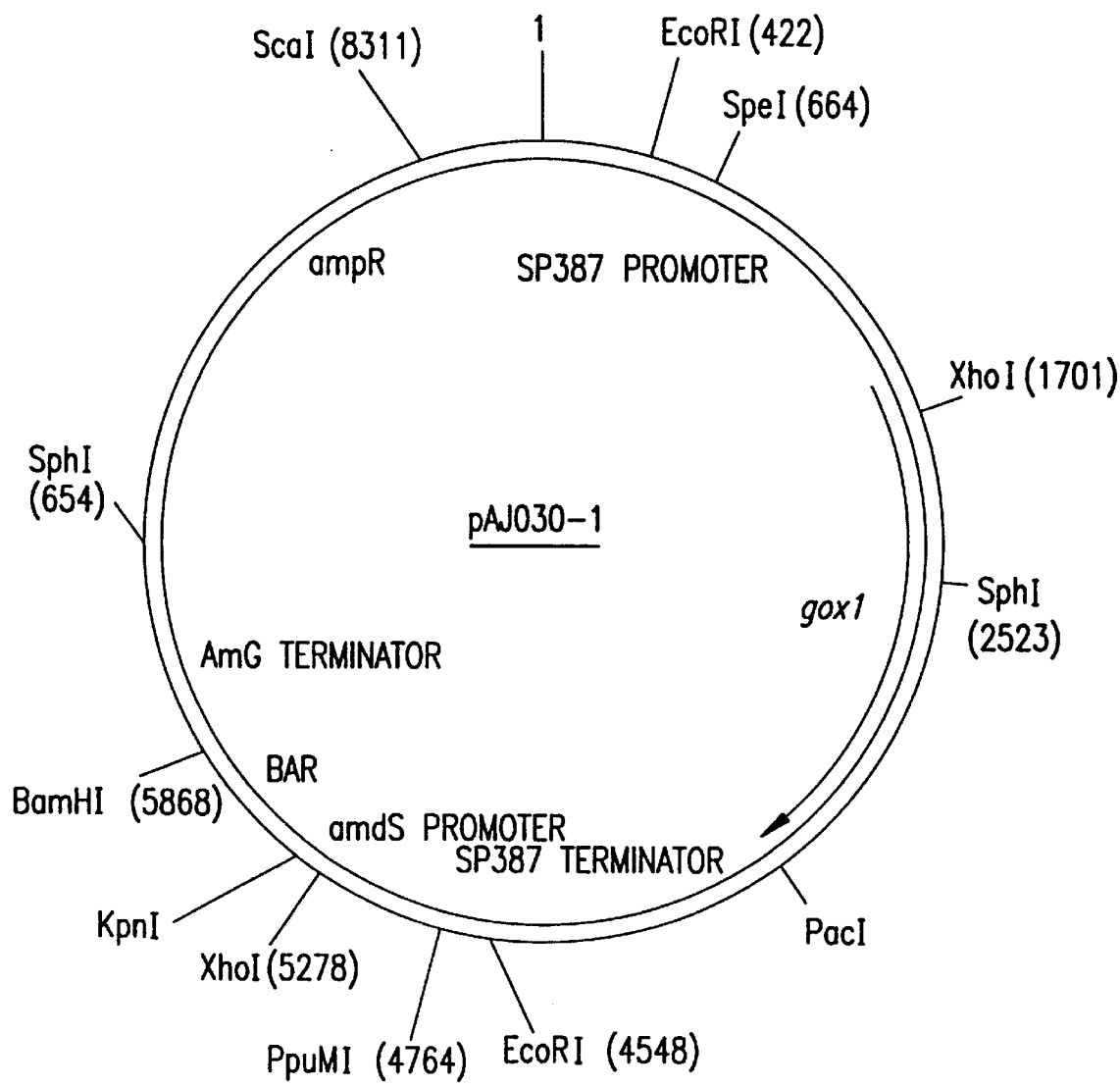
FIG. 7 shows the restriciton map of pAJ030-1.

The resulting 2.3 kb fragment minus the TAKA Na2-tpi promoter and the AMG terminator is subcloned into pBANe6 (FIG. 4). This is accomplished by digesting the PCR fragment with XhoI and NsiI and ligating it into pBANe6 which is digested with SalI and partially digested with NsiI to cut the NsiI 1524 bp down stream the SalI site and band purifying the digest to remove the TAKA Na2-tpi promoter and the amdS terminator. The resulting plasmid, pDM174.3, is digested with EcoRI to remove a fragment containing the trypsin gene promoter, the polylinker (SwaI, KpnI, and PacI) and the *Fusarium oxysporum* trypsin gene terminator and ligating it into pMT1612 (FIG. 5) which contains the *Streptomyces hygroscopicus* bar gene (Thompson et al., 1987, *EMBO Journal* 6: 2519–2513). The resulting plasmid is digested with EcoRI and band purified to remove the amdS and AMG fragment to produce pDM181 FIG. 6).

6.8. Construction of the *Cladsporium oxysporum* glucose oxidase gene expression plasmid pAJ030-1

To create a *Cladsporium oxysporum* glucose oxidase gene (gox1) expression plasmid for use in a Fusarium strain, complementary sense (GOXpcr1), and antisense (GOXpcr-2) primers are designed to the flanking 5' and 3' ends of the coding region of gox1 and used to amplify the genomic coding region by PCR.

GOXpcr1: 5'-dCCACCATGTACAAACCCATCGCGC-3' (SEQ ID NO:27)

PacI
GOXpcr-2: 5'-dCCCTTAATTAACGCTCATCACGCCCTCTGATCCTC-3' (SEQ ID NO:28)

The 50 μl PCR reaction contains 1× pwo DNA polymerase buffer, 200 μM each of dATP, dCTP, dGTP, and dTTP, approximately 200 ng of *Cladosporium oxysporum* genomic A4591 DNA, and 50 pmol of each primer. Five units of Pwo DNA polymerase are added after the reaction is incubated for 3 minutes at 95° C. The reaction is then incubated for 30 cycles each at 95° C. for 30 seconds, 57° C. for 1 minute, and 72° C. for 1 minute. Following the last cycle, the reaction is incubated at 72° C. for 5 minutes. The resulting 1.8 kb PCR product is gel purified using a Qia Quick Spin column, is digested with PacI, and is cloned into pDM181 (FIG. 6) which is digested with SwaI and Pac( to create pAJ030-1 (FIG. 7). The veracity of the gox1 gene in pAJ030-1 is verified by sequencing with an Applied Biosystems Model 373A Automated DNA sequencer.

6.9. Transformation of pAJ030-1 into Fusarium strain A3/5 CC-I

Fusarium strain A3/5 CC1-3 (Wiebe et al., 1992, *Mycological Research* 96: 555–562; Wiebe et al., 1991, *Mycological Research* 95: 1284–1288; Wiebe et al., 1991, *Mycological Research* 96: 555–562) protoplasting and transformation are performed according to Royer et al., 1995, supra. Five μg of pAJ030-1 plasmid DNA is used in the transformation. One ml of SPTC (0.8M sorbitol-40% polyethylene glycol 4000-50 mM $CaCl_2$-50 mM Tris pH 8) is mixed gently into the protoplast suspension and incubation is continued at room temperature for 20 minutes. Twenty five ml of molten solution (cooled to 40° C.) consisting of COVE salts, 25 mM NaNO3, 0.8M sucrose and 1% low melting agarose (Sigma Chemical Company, St. Louis, Mo.) are mixed with the protoplasts and then plated onto an empty 150 mm petri plate. Incubation is continued at room temperature for 10 to 14 days. After incubation at room temperature for 24 hours, 25 ml of the identical medium plus basta (5 mg/ml) are overlayed onto the petri plate. Basta is obtained from AgrEvo (Hoechst Schering, Rodovre, Denmark) and is extracted twice with phenol:chloroform:isoamyl alcohol (25:24:1), and once with chloroform:isoamyl alcohol (24:1) before use. The COVE salts solution is composed of 26 g of KCl, 26 g of $MgSO_4$-$7H_2O$, 76 g of $KH_2PO_4$, and 50 ml of COVE trace metals per liter. The COVE trace metals solution is composed of 0.04 g of $Na_2B_4O_7$-$10H_2O$, 0.4 g of $CuSO_4$-$5H_2O$, 1.2 g of $FeSO_4$-$7H_2O$, 0.07 g of $MnSO_4$-$H_2O$, 0.8 g of $Na_2MoO_2$-$2H_2O$, and 10 g of $ZnSO_4$-$7H_2O$ per liter.

Primary transformants are inoculated into 25 ml of M400Da pH 6.0 medium composed of 50 g of maltodextrin, 2 g of $MgSO_4$-$7H_2O$, 2 g of $KH_2PO_4$, 4 g of citric acid, 8 g of yeast extract, 2 g of urea, and 1 ml of COVE trace metals per liter. The transformants are grown for 7 days at 30° C. with shaking at 150 rpm.

Transformation of Fusarium strain A3/5 CC-1 with pAJ030-1 results in 7 primary transformants.

6.9 Expression of the *Cladosporium oxysporum* glucose oxidase gene in Fusarium strain A3/5 CC-1

The seven transformants are grown in 125 ml baffled shake flasks containing 25 ml of M400D at 30° C. with shaking at 150 rpm. After 7 days, culture broths are assayed for GOX activity.

Seven day culture broth is diluted 1:300, 1:600 and 1:1200 in 100 mM sodium acetate pH 5.6 buffer and 20 μl of each dilution is transferred to a microtiter dish. To begin the reaction 200 μl of GOX substrate buffer (100 mM sodium acetate pH 5.6, 100 mM D-glucose, 0.4 mM ABTS and 0.3 POXU/ml of *Coprinus cinereus* peroxidase is added. After 20 minutes at 20° C., color development is measured using a micro plate reader at 405 nm. GOX activity is determined by comparison to standards of *Aspergillus niger* glucose oxidase (Sigma Chemical Co., St. Louis, Mo.). To confirm that observed activities are glucose dependent, diluted broths are also assayed with GOX substrate buffer lacking D-glucose.

All 7 transformants are found to produce detectable glucose oxidase activity. When the samples are re-assayed in GOX substrate buffer lacking glucose, color development is not detected indicating that the activities observed are glucose dependent.

7. DEPOSIT OF MICROORGANISMS

The following biological materials have been deposited in the Agricultural Research Service Patent Culture Collection (NRRL), Northern Regional Research Center, 1815 University Street, Peoria, Ill., 61604, USA.

| Strain | Accession No. | Deposit Date |
|---|---|---|
| *E. coli* containing pGOX4A | NRRL B-21628 | 10/11/96 |
| *E. coli* containing pGOX6A | NRRL B-21629 | 10/11/96 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
( A ) LENGTH: 613 amino acids
( B ) TYPE: amino acid
( C ) STRANDEDNESS: single
( D ) TOPOLOGY: linear ( x i ) SEQUENCE DESCRIPTION: SEQ ID NO:1:

```
Met Tyr Lys Pro Ile Ala Leu Ser Thr Leu Leu Ala Val Ala Ser Gln
  1               5                  10                  15

Ala Leu Pro His Gln Ser Arg Ala Glu Ser Ala His Ala Ile Thr Ala
                 20                  25                  30

Asp Val Ser Gln Val Ser Asn Lys Thr Phe Asp Tyr Ile Val Cys Gly
             35                  40                  45

Gly Gly Leu Thr Gly Leu Val Ala Ser Arg Leu Ser Glu Asp Pro
 50                      55                  60

Asn Ile Ser Val Leu Val Ile Glu Gly Gly Asn Asp Asp His Glu Asp
 65                      70                  75                  80

Pro Arg Val Asn Asp Val Arg Thr Tyr Gly Gln Ala Phe Glu Thr Glu
                     85                  90                  95

Leu Asp Tyr Gly Leu Lys Ser Thr Ser Val Pro Trp Gln Asn Asn Thr
                100                 105                 110

Gly Leu Leu Leu Val Ala Gly Lys Thr Leu Gly Gly Ser Gly Ser Ile
            115                 120                 125

Asn Gly Ala Ser Trp Thr Lys Gly Asp Lys Thr Gln Tyr Asp Leu Leu
 130                    135                 140

Pro Gly Leu Thr Gly Asp Asp Ser Trp Ser Phe Asp Ala Leu Asn Glu
 145                    150                 155                 160

Ile Met Leu Ser Ile Glu Asp Phe His Thr Pro Thr Glu Asp Gln Val
                165                 170                 175

Ala Lys Gly Ala Ala Phe Glu Gly Glu Phe His Gly Arg Glu Gly Asn
                180                 185                 190

Val Gln Val Ser Phe Pro Ala Gly Met Phe Gly Ser Ile Gln Gln Pro
            195                 200                 205

Ala Leu Glu Ala Ser Ala Leu Val Trp Lys Gly Met Lys Lys Val Ala
 210                    215                 220

Asp Phe Ala Ala Gly Ile Thr Thr Gly Ala Thr Met Ile Pro Asn Met
 225                    230                 235                 240

Leu Glu Ala Asn Glu Ser Gln Asn Arg Ser Ser Pro Phe Thr Val Tyr
                245                 250                 255

Ala Lys Gln Gln Thr Gln Glu Arg Asp Asn Phe Ile Ile Leu Thr Gly
                260                 265                 270

His Arg Val Ile Ser Leu Asn Trp Arg Glu Gly Ser Glu Met Ile Ala
            275                 280                 285

Asp Gly Val Ser Phe Gln Ala Cys Arg Asp Cys Lys Ile His Lys Ala
 290                    295                 300

Lys Thr Lys Arg Glu Val Leu Leu Ala Gly Gly Ser Leu Gln Ser Pro
 305                    310                 315                 320

Gln Leu Leu Glu Leu Ser Gly Val Gly Asn Pro Asp Val Leu Ala Ala
                325                 330                 335
```

| | | | | | | | | | | | | | | |
|---|---|---|---|---|---|---|---|---|---|---|---|---|---|---|
|Ala|Ala|Val|Pro 340|Leu|Lys|Leu|Ala|Ser 345|Pro|Asn|Val|Gly|Lys 350|Asn|Met|
|Gln|Glu|Gln 355|Thr|Lys|Asn|Thr|Leu 360|Trp|Phe|Asp|Pro|Val 365|Asn|Thr|Glu|
|Phe|Asp 370|Gly|Ser|Gly|Pro|Pro 375|Asn|Ala|Ile|Ser|Phe 380|Pro|Asn|Val|Asp|
|Gln 385|Leu|Phe|Arg|Asn|Asn 390|Ser|Ala|Thr|Met|Tyr 395|Lys|Asn|Ile|Met|Ser 400|
|Gly|Leu|Lys|Gln|Tyr 405|Ser|Glu|Asp|Leu|Ala 410|Ala|Thr|Gly|Thr|Val 415|Thr|
|Asn|Ala|Thr|Ala 420|Thr|His|Gln|Ile|Leu 425|Glu|Ala|Gln|Val|Asp 430|Asn|Leu|
|Trp|His|Asn 435|Leu|Val|Gly|Ala|Ala 440|Glu|Ile|Phe|Phe|Val 445|Thr|Ser|Pro|
|Ala|Thr 450|Gly|Gln|Val|Gly|Val 455|Asp|Leu|Trp|Asn|Leu 460|Ile|Val|Leu|Ser|
|Arg 465|Gly|Tyr|Val|His|Ile 470|Thr|Ser|Asn|Ser|Ser 475|Trp|Asp|His|Pro|Glu 480|
|Ile|Glu|Pro|Ser|Tyr 485|Phe|Gly|His|Gln|Phe 490|Asp|Leu|Asp|Val|Gln 495|Leu|
|Ala|Ala|Thr|Lys 500|Gln|Ser|Arg|Glu|Val 505|Phe|Gln|Thr|Asp|Pro 510|Leu|Ala|
|Pro|Leu|Val 515|Ser|Ala|Glu|Thr|Phe 520|Pro|Gly|Leu|Glu|Ala 525|Val|Pro|Gln|
|Gly|Ala 530|Glu|Asp|Gln|Val|Trp 535|Glu|Gln|Trp|Val|Lys 540|Ala|Thr|Phe|Thr|
|Ser 545|Val|Trp|His|Tyr|Ile 550|Ala|Thr|Leu|Gly|Met 555|Met|Lys|Glu|Glu|Leu 560|
|Gly|Gly|Val|Val|Asp 565|Ser|Arg|Leu|Lys|Val 570|Tyr|Gly|Ile|Glu|Asn 575|Val|
|Arg|Ala|Val|Asp 580|Ala|Ser|Val|Leu|Pro 585|Ile|Gln|Leu|Ser|Ala 590|His|Leu|
|Ser|Ser|Ser 595|Leu|Tyr|Gly|Ile|Ala 600|Glu|Lys|Ala|Ala|Lys 605|Met|Ile|Lys|
|Glu|Asp 610|Gln|Arg|Ala| | | | | | | | | | | |

( 2 ) INFORMATION FOR SEQ ID NO:2:

( i ) SEQUENCE CHARACTERISTICS:
        ( A ) LENGTH: 2386 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: Coding Sequence
        ( B ) LOCATION: 351...2189
        ( D ) OTHER INFORMATION:

( x i ) SEQUENCE DESCRIPTION: SEQ ID NO:2:

| | | | | | |
|---|---|---|---|---|---|
|CAACGTCACT|GCTGAGGCTG|TGACACCTCT|GGCCGAGCCA|ATCCGCACAA|CGTGCTCGCC|60|
|CACGAACGCC|AACACGGACC|CTGATGTTAT|CTTTTTGAAG|ATGACAATAC|CCTGCCAAGC|120|
|ACATAAGTCT|GCCCTAATGA|TCCATCGAGA|CAGACATCTT|CATGACATTT|CGTTGAGGTC|180|
|AAGCCAAGCA|AGACGGTGCG|TGAGCACGTT|GCATACTACG|TACTCGCAAC|CGCACGTATT|240|

-continued

| | | | | | | | | | | | | | | | | |
|---|---|---|---|---|---|---|---|---|---|---|---|---|---|---|---|---|
| GCGATACTGT | | | GCTCTTTGAG | | | AAAGACATAA | | | GTAGACGGTA | | | GCAGAATCGC | | | ATTTCCGGGC | 300 |

| | | | | | | | | | | | | | | | |
|---|---|---|---|---|---|---|---|---|---|---|---|---|---|---|---|
| TTCCTTTCCT | | | CAGCATCCAC | | | CAACTCAGAC | | | TCGCCTCATC | | | TTGAGCCATC | ATG | TAC | 356 |
| | | | | | | | | | | | | | Met | Tyr | |
| | | | | | | | | | | | | | 1 | | |

| AAA | CCC | ATC | GCG | CTT | TCC | ACT | CTA | CTC | GCT | GTT | GCC | TCA | CAG | GCA | CTG | 404 |
|---|---|---|---|---|---|---|---|---|---|---|---|---|---|---|---|---|
| Lys | Pro | Ile | Ala | Leu | Ser | Thr | Leu | Leu | Ala | Val | Ala | Ser | Gln | Ala | Leu | |
| | | 5 | | | | 10 | | | | | 15 | | | | | |

| CCA | CAC | CAA | TCT | CGA | GCC | GAG | AGC | GCC | CAC | GCA | ATT | ACA | GCA | GAC | GTC | 452 |
|---|---|---|---|---|---|---|---|---|---|---|---|---|---|---|---|---|
| Pro | His | Gln | Ser | Arg | Ala | Glu | Ser | Ala | His | Ala | Ile | Thr | Ala | Asp | Val | |
| | 20 | | | | 25 | | | | | 30 | | | | | | |

| TCC | CAA | GTC | TCA | AAC | AAG | ACC | TTC | GAC | TAC | ATC | GTC | TGT | GGA | GGC | GGG | 500 |
|---|---|---|---|---|---|---|---|---|---|---|---|---|---|---|---|---|
| Ser | Gln | Val | Ser | Asn | Lys | Thr | Phe | Asp | Tyr | Ile | Val | Cys | Gly | Gly | Gly | |
| 35 | | | | 40 | | | | | 45 | | | | | 50 | | |

| CTC | ACA | GGC | TTA | GTC | GTC | GCA | AGC | CGC | TTG | TCC | GAA | GAT | CCA | AAC | ATC | 548 |
|---|---|---|---|---|---|---|---|---|---|---|---|---|---|---|---|---|
| Leu | Thr | Gly | Leu | Val | Val | Ala | Ser | Arg | Leu | Ser | Glu | Asp | Pro | Asn | Ile | |
| | | | | 55 | | | | 60 | | | | | 65 | | | |

| TCC | GTT | CTG | GTG | ATC | GAG | GGT | GGC | AAC | GAC | GAC | CAC | GAA | GAC | CCT | CGG | 596 |
|---|---|---|---|---|---|---|---|---|---|---|---|---|---|---|---|---|
| Ser | Val | Leu | Val | Ile | Glu | Gly | Gly | Asn | Asp | Asp | His | Glu | Asp | Pro | Arg | |
| | | | 70 | | | | | 75 | | | | | 80 | | | |

| GTT | AAC | GAC | GTG | AGG | ACT | TAC | GGA | CAA | GCC | TTC | GAG | ACC | GAA | CTC | GAC | 644 |
|---|---|---|---|---|---|---|---|---|---|---|---|---|---|---|---|---|
| Val | Asn | Asp | Val | Arg | Thr | Tyr | Gly | Gln | Ala | Phe | Glu | Thr | Glu | Leu | Asp | |
| | | 85 | | | | | 90 | | | | | 95 | | | | |

| TAT | GGC | CTC | AAA | TCC | ACT | TCA | GTT | CCA | TGG | CAG | AAC | AAC | ACC | GGT | CTC | 692 |
|---|---|---|---|---|---|---|---|---|---|---|---|---|---|---|---|---|
| Tyr | Gly | Leu | Lys | Ser | Thr | Ser | Val | Pro | Trp | Gln | Asn | Asn | Thr | Gly | Leu | |
| | 100 | | | | | 105 | | | | | 110 | | | | | |

| CTG | CTT | GTC | GCA | GGC | AAG | ACT | CTT | GGT | GGG | AGT | GGC | AGC | ATC | AAC | GGC | 740 |
|---|---|---|---|---|---|---|---|---|---|---|---|---|---|---|---|---|
| Leu | Leu | Val | Ala | Gly | Lys | Thr | Leu | Gly | Gly | Ser | Gly | Ser | Ile | Asn | Gly | |
| 115 | | | | | 120 | | | | | 125 | | | | | 130 | |

| GCC | AGC | TGG | ACC | AAA | GGC | GAC | AAG | ACT | CAG | TAT | GAT | CTC | CTC | CCC | GGT | 788 |
|---|---|---|---|---|---|---|---|---|---|---|---|---|---|---|---|---|
| Ala | Ser | Trp | Thr | Lys | Gly | Asp | Lys | Thr | Gln | Tyr | Asp | Leu | Leu | Pro | Gly | |
| | | | | 135 | | | | | 140 | | | | | 145 | | |

| TTG | ACT | GGC | GAC | GAT | TCC | TGG | TCC | TTC | GAC | GCC | CTC | AAC | GAG | ATC | ATG | 836 |
|---|---|---|---|---|---|---|---|---|---|---|---|---|---|---|---|---|
| Leu | Thr | Gly | Asp | Asp | Ser | Trp | Ser | Phe | Asp | Ala | Leu | Asn | Glu | Ile | Met | |
| | | | 150 | | | | | 155 | | | | | 160 | | | |

| CTC | AGT | ATT | GAG | GAC | TTC | CAC | ACC | CCA | ACT | GAG | GAC | CAA | GTA | GCC | AAA | 884 |
|---|---|---|---|---|---|---|---|---|---|---|---|---|---|---|---|---|
| Leu | Ser | Ile | Glu | Asp | Phe | His | Thr | Pro | Thr | Glu | Asp | Gln | Val | Ala | Lys | |
| | | 165 | | | | | 170 | | | | | 175 | | | | |

| GGT | GCT | GCA | TTT | GAA | GGA | GAG | TTT | CAT | GGA | CGC | GAG | GGC | AAT | GTT | CAA | 932 |
|---|---|---|---|---|---|---|---|---|---|---|---|---|---|---|---|---|
| Gly | Ala | Ala | Phe | Glu | Gly | Glu | Phe | His | Gly | Arg | Glu | Gly | Asn | Val | Gln | |
| | 180 | | | | | 185 | | | | | 190 | | | | | |

| GTG | TCC | TTC | CCT | GCG | GGC | ATG | TTT | GGC | AGC | ATA | CAG | CAA | CCA | GCT | CTG | 980 |
|---|---|---|---|---|---|---|---|---|---|---|---|---|---|---|---|---|
| Val | Ser | Phe | Pro | Ala | Gly | Met | Phe | Gly | Ser | Ile | Gln | Gln | Pro | Ala | Leu | |
| 195 | | | | | 200 | | | | | 205 | | | | | 210 | |

| GAG | GCA | TCC | GCT | CTC | GTC | TGG | AAG | GGC | ATG | AAG | AAA | GTT | GCC | GAC | TTC | 1028 |
|---|---|---|---|---|---|---|---|---|---|---|---|---|---|---|---|---|
| Glu | Ala | Ser | Ala | Leu | Val | Trp | Lys | Gly | Met | Lys | Lys | Val | Ala | Asp | Phe | |
| | | | | 215 | | | | | 220 | | | | | 225 | | |

| GCG | GCC | GGT | ATC | ACG | ACT | GGT | GCG | ACC | ATG | ATT | CCC | AAC | ATG | CTT | GAG | 1076 |
|---|---|---|---|---|---|---|---|---|---|---|---|---|---|---|---|---|
| Ala | Ala | Gly | Ile | Thr | Thr | Gly | Ala | Thr | Met | Ile | Pro | Asn | Met | Leu | Glu | |
| | | | | 230 | | | | | 235 | | | | | 240 | | |

| GCC | AAT | GAG | TCC | CAG | AAC | CGC | TCC | TCA | CCT | TTC | ACG | GTT | TAC | GCC | AAG | 1124 |
|---|---|---|---|---|---|---|---|---|---|---|---|---|---|---|---|---|
| Ala | Asn | Glu | Ser | Gln | Asn | Arg | Ser | Ser | Pro | Phe | Thr | Val | Tyr | Ala | Lys | |
| | | 245 | | | | | 250 | | | | | 255 | | | | |

| CAG | CAA | ACA | CAA | GAG | CGC | GAT | AAC | TTC | ATC | ATC | CTC | ACG | GGA | CAC | CGT | 1172 |
|---|---|---|---|---|---|---|---|---|---|---|---|---|---|---|---|---|
| Gln | Gln | Thr | Gln | Glu | Arg | Asp | Asn | Phe | Ile | Ile | Leu | Thr | Gly | His | Arg | |
| | 260 | | | | | 265 | | | | | 270 | | | | | |

| GTG | ATC | TCT | CTC | AAC | TGG | CGC | GAG | GGC | TCC | GAA | ATG | ATC | GCC | GAT | GGC | 1220 |
|---|---|---|---|---|---|---|---|---|---|---|---|---|---|---|---|---|
| Val | Ile | Ser | Leu | Asn | Trp | Arg | Glu | Gly | Ser | Glu | Met | Ile | Ala | Asp | Gly | |
| 275 | | | | | 280 | | | | | 285 | | | | | 290 | |

| GTC | AGC | TTC | CAG | GCA | TGC | CGT | GAC | TGC | AAA | ATC | CAC | AAG | GCC | AAG | ACA | 1268 |

```
              Val  Ser  Phe  Gln  Ala  Cys  Arg  Asp  Cys  Lys  Ile  His  Lys  Ala  Lys  Thr
                                  295                      300                      305

AAG  CGA  GAA  GTG  CTT  CTT  GCT  GGC  GGC  TCT  TTG  CAA  AGC  CCA  CAG  CTA          1316
Lys  Arg  Glu  Val  Leu  Leu  Ala  Gly  Gly  Ser  Leu  Gln  Ser  Pro  Gln  Leu
               310                      315                      320

CTT  GAG  CTT  TCT  GGA  GTA  GGC  AAC  CCC  GAT  GTA  CTG  GCA  GCC  GCC  GCC          1364
Leu  Glu  Leu  Ser  Gly  Val  Gly  Asn  Pro  Asp  Val  Leu  Ala  Ala  Ala  Ala
               325                      330                      335

GTG  CCG  CTC  AAA  TTG  GCG  TCT  CCA  AAC  GTT  GGC  AAA  AAC  ATG  CAA  GAG          1412
Val  Pro  Leu  Lys  Leu  Ala  Ser  Pro  Asn  Val  Gly  Lys  Asn  Met  Gln  Glu
               340                      345                      350

CAA  ACC  AAG  AAC  ACC  CTC  TGG  TTC  GAT  CCC  GTC  AAC  ACC  GAG  TTC  GAT          1460
Gln  Thr  Lys  Asn  Thr  Leu  Trp  Phe  Asp  Pro  Val  Asn  Thr  Glu  Phe  Asp
355                      360                      365                      370

GGT  TCT  GGA  CCA  CCC  AAC  GCC  ATC  TCT  TTC  CCG  AAT  GTC  GAT  CAG  TTG          1508
Gly  Ser  Gly  Pro  Pro  Asn  Ala  Ile  Ser  Phe  Pro  Asn  Val  Asp  Gln  Leu
                    375                      380                      385

TTC  AGG  AAT  AAC  AGC  GCC  ACC  ATG  TAC  AAG  AAC  ATC  ATG  TCT  GGC  CTC          1556
Phe  Arg  Asn  Asn  Ser  Ala  Thr  Met  Tyr  Lys  Asn  Ile  Met  Ser  Gly  Leu
               390                      395                      400

AAG  CAA  TAC  TCA  GAA  GAC  CTG  GCC  GCT  ACC  GGC  ACG  GTG  ACC  AAC  GCC          1604
Lys  Gln  Tyr  Ser  Glu  Asp  Leu  Ala  Ala  Thr  Gly  Thr  Val  Thr  Asn  Ala
          405                      410                      415

ACA  GCC  ACC  CAC  CAG  ATC  CTC  GAA  GCA  CAG  GTC  GAC  AAC  CTC  TGG  CAC          1652
Thr  Ala  Thr  His  Gln  Ile  Leu  Glu  Ala  Gln  Val  Asp  Asn  Leu  Trp  His
420                      425                      430

AAC  CTT  GTA  GGC  GCC  GCC  GAA  ATC  TTC  TTC  GTG  ACA  TCA  CCC  GCC  ACC          1700
Asn  Leu  Val  Gly  Ala  Ala  Glu  Ile  Phe  Phe  Val  Thr  Ser  Pro  Ala  Thr
435                      440                      445                      450

GGC  CAA  GTC  GGC  GTC  GAC  CTC  TGG  AAC  CTG  ATC  GTT  TTG  TCG  CGT  GGC          1748
Gly  Gln  Val  Gly  Val  Asp  Leu  Trp  Asn  Leu  Ile  Val  Leu  Ser  Arg  Gly
                    455                      460                      465

TAT  GTG  CAC  ATC  ACC  TCA  AAC  TCC  TCA  TGG  GAT  CAC  CCA  GAA  ATC  GAG          1796
Tyr  Val  His  Ile  Thr  Ser  Asn  Ser  Ser  Trp  Asp  His  Pro  Glu  Ile  Glu
               470                      475                      480

CCT  TCC  TAC  TTC  GGT  CAC  CAA  TTC  GAC  CTC  GAC  GTC  CAA  CTA  GCA  GCG          1844
Pro  Ser  Tyr  Phe  Gly  His  Gln  Phe  Asp  Leu  Asp  Val  Gln  Leu  Ala  Ala
          485                      490                      495

ACC  AAG  CAG  TCG  CGC  GAA  GTC  TTC  CAG  ACC  GAC  CCT  CTA  GCT  CCT  CTC          1892
Thr  Lys  Gln  Ser  Arg  Glu  Val  Phe  Gln  Thr  Asp  Pro  Leu  Ala  Pro  Leu
500                      505                      510

GTC  AGC  GCT  GAG  ACT  TTC  CCG  GGC  CTT  GAA  GCC  GTG  CCG  CAA  GGC  GCA          1940
Val  Ser  Ala  Glu  Thr  Phe  Pro  Gly  Leu  Glu  Ala  Val  Pro  Gln  Gly  Ala
515                      520                      525                      530

GAA  GAT  CAG  GTC  TGG  GAG  CAG  TGG  GTC  AAA  GCC  ACC  TTC  ACC  TCT  GTC          1988
Glu  Asp  Gln  Val  Trp  Glu  Gln  Trp  Val  Lys  Ala  Thr  Phe  Thr  Ser  Val
                    535                      540                      545

TGG  CAC  TAC  ATC  GCA  ACC  TTG  GGT  ATG  ATG  AAG  GAG  GAA  CTT  GGA  GGC          2036
Trp  His  Tyr  Ile  Ala  Thr  Leu  Gly  Met  Met  Lys  Glu  Glu  Leu  Gly  Gly
               550                      555                      560

GTC  GTG  GAC  AGC  AGA  TTG  AAG  GTC  TAC  GGT  ATT  GAG  AAT  GTG  CGT  GCT          2084
Val  Val  Asp  Ser  Arg  Leu  Lys  Val  Tyr  Gly  Ile  Glu  Asn  Val  Arg  Ala
          565                      570                      575

GTG  GAT  GCT  AGC  GTG  TTG  CCG  ATT  CAG  CTT  TCG  GCG  CAT  CTT  AGT  TCT          2132
Val  Asp  Ala  Ser  Val  Leu  Pro  Ile  Gln  Leu  Ser  Ala  His  Leu  Ser  Ser
580                      585                      590

TCG  CTG  TAT  GGC  ATT  GCT  GAG  AAG  GCT  GCG  AAG  ATG  ATC  AAG  GAG  GAT          2180
Ser  Leu  Tyr  Gly  Ile  Ala  Glu  Lys  Ala  Ala  Lys  Met  Ile  Lys  Glu  Asp
595                      600                      605                      610

CAG  AGG  GCG  TGATTAGCGT  TCTAAAACAA  TCATGATAGC  ATGTTTGAGT  GGCATGCTC              2238
```

```
Gln  Arg  Ala

ATTGCAGCTC  TGGGCGGAAT  TTTGTGGCTC  TGCTAATAAG  GAGTCCTTGG  CTTAAGTATG    2298

CACTCACACC  AACATTTTAT  CTACATCGCT  TAGTAGCGAT  GATGTACGAA  TCCACATCCA    2358

ATCAGTCCAA  TCATCGTATA  AGTCTGTC                                          2386
```

( 2 ) INFORMATION FOR SEQ ID NO:3:

( i ) SEQUENCE CHARACTERISTICS:
        ( A ) LENGTH: 1839 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: Coding Sequence
        ( B ) LOCATION: 1...1839
        ( D ) OTHER INFORMATION:

( x i ) SEQUENCE DESCRIPTION: SEQ ID NO:3:

```
ATG  TAC  AAA  CCC  ATC  GCG  CTT  TCC  ACT  CTA  CTC  GCT  GTT  GCC  TCA  CAG     48
Met  Tyr  Lys  Pro  Ile  Ala  Leu  Ser  Thr  Leu  Leu  Ala  Val  Ala  Ser  Gln
 1                   5                        10                       15

GCA  CTG  CCA  CAC  CAA  TCT  CGA  GCC  GAG  AGC  GCC  CAC  GCA  ATT  ACA  GCA     96
Ala  Leu  Pro  His  Gln  Ser  Arg  Ala  Glu  Ser  Ala  His  Ala  Ile  Thr  Ala
               20                       25                       30

GAC  GTC  TCC  CAA  GTC  TCA  AAC  AAG  ACC  TTC  GAC  TAC  ATC  GTC  TGT  GGA    144
Asp  Val  Ser  Gln  Val  Ser  Asn  Lys  Thr  Phe  Asp  Tyr  Ile  Val  Cys  Gly
                    35                        40                       45

GGC  GGG  CTC  ACA  GGC  TTA  GTC  GTC  GCA  AGC  CGC  TTG  TCC  GAA  GAT  CCA    192
Gly  Gly  Leu  Thr  Gly  Leu  Val  Val  Ala  Ser  Arg  Leu  Ser  Glu  Asp  Pro
 50                      55                       60

AAC  ATC  TCC  GTT  CTG  GTG  ATC  GAG  GGT  GGC  AAC  GAC  GAC  CAC  GAA  GAC    240
Asn  Ile  Ser  Val  Leu  Val  Ile  Glu  Gly  Gly  Asn  Asp  Asp  His  Glu  Asp
 65                      70                       75                       80

CCT  CGG  GTT  AAC  GAC  GTG  AGG  ACT  TAC  GGA  CAA  GCC  TTC  GAG  ACC  GAA    288
Pro  Arg  Val  Asn  Asp  Val  Arg  Thr  Tyr  Gly  Gln  Ala  Phe  Glu  Thr  Glu
                         85                       90                       95

CTC  GAC  TAT  GGC  CTC  AAA  TCC  ACT  TCA  GTT  CCA  TGG  CAG  AAC  AAC  ACC    336
Leu  Asp  Tyr  Gly  Leu  Lys  Ser  Thr  Ser  Val  Pro  Trp  Gln  Asn  Asn  Thr
                    100                      105                      110

GGT  CTC  CTG  CTT  GTC  GCA  GGC  AAG  ACT  CTT  GGT  GGG  AGT  GGC  AGC  ATC    384
Gly  Leu  Leu  Leu  Val  Ala  Gly  Lys  Thr  Leu  Gly  Gly  Ser  Gly  Ser  Ile
               115                      120                      125

AAC  GGC  GCC  AGC  TGG  ACC  AAA  GGC  GAC  AAG  ACT  CAG  TAT  GAT  CTC  CTC    432
Asn  Gly  Ala  Ser  Trp  Thr  Lys  Gly  Asp  Lys  Thr  Gln  Tyr  Asp  Leu  Leu
     130                      135                      140

CCC  GGT  TTG  ACT  GGC  GAC  GAT  TCC  TGG  TCC  TTC  GAC  GCC  CTC  AAC  GAG    480
Pro  Gly  Leu  Thr  Gly  Asp  Asp  Ser  Trp  Ser  Phe  Asp  Ala  Leu  Asn  Glu
145                      150                      155                      160

ATC  ATG  CTC  AGT  ATT  GAG  GAC  TTC  CAC  ACC  CCA  ACT  GAG  GAC  CAA  GTA    528
Ile  Met  Leu  Ser  Ile  Glu  Asp  Phe  His  Thr  Pro  Thr  Glu  Asp  Gln  Val
                    165                      170                      175

GCC  AAA  GGT  GCT  GCA  TTT  GAA  GGA  GAG  TTT  CAT  GGA  CGC  GAG  GGC  AAT    576
Ala  Lys  Gly  Ala  Ala  Phe  Glu  Gly  Glu  Phe  His  Gly  Arg  Glu  Gly  Asn
               180                      185                      190

GTT  CAA  GTG  TCC  TTC  CCT  GCG  GGC  ATG  TTT  GGC  AGC  ATA  CAG  CAA  CCA    624
Val  Gln  Val  Ser  Phe  Pro  Ala  Gly  Met  Phe  Gly  Ser  Ile  Gln  Gln  Pro
          195                      200                      205

GCT  CTG  GAG  GCA  TCC  GCT  CTC  GTC  TGG  AAG  GGC  ATG  AAG  AAA  GTT  GCC    672
Ala  Leu  Glu  Ala  Ser  Ala  Leu  Val  Trp  Lys  Gly  Met  Lys  Lys  Val  Ala
```

```
            210                       215                       220
GAC  TTC  GCG  GCC  GGT  ATC  ACG  ACT  GGT  GCG  ACC  ATG  ATT  CCC  AAC  ATG     720
Asp  Phe  Ala  Ala  Gly  Ile  Thr  Thr  Gly  Ala  Thr  Met  Ile  Pro  Asn  Met
225                 230                      235                      240

CTT  GAG  GCC  AAT  GAG  TCC  CAG  AAC  CGC  TCC  TCA  CCT  TTC  ACG  GTT  TAC     768
Leu  Glu  Ala  Asn  Glu  Ser  Gln  Asn  Arg  Ser  Ser  Pro  Phe  Thr  Val  Tyr
                    245                      250                      255

GCC  AAG  CAG  CAA  ACA  CAA  GAG  CGC  GAT  AAC  TTC  ATC  ATC  CTC  ACG  GGA     816
Ala  Lys  Gln  Gln  Thr  Gln  Glu  Arg  Asp  Asn  Phe  Ile  Ile  Leu  Thr  Gly
               260                      265                      270

CAC  CGT  GTG  ATC  TCT  CTC  AAC  TGG  CGC  GAG  GGC  TCC  GAA  ATG  ATC  GCC     864
His  Arg  Val  Ile  Ser  Leu  Asn  Trp  Arg  Glu  Gly  Ser  Glu  Met  Ile  Ala
          275                      280                      285

GAT  GGC  GTC  AGC  TTC  CAG  GCA  TGC  CGT  GAC  TGC  AAA  ATC  CAC  AAG  GCC     912
Asp  Gly  Val  Ser  Phe  Gln  Ala  Cys  Arg  Asp  Cys  Lys  Ile  His  Lys  Ala
290                      295                      300

AAG  ACA  AAG  CGA  GAA  GTG  CTT  CTT  GCT  GGC  GGC  TCT  TTG  CAA  AGC  CCA     960
Lys  Thr  Lys  Arg  Glu  Val  Leu  Leu  Ala  Gly  Gly  Ser  Leu  Gln  Ser  Pro
305                      310                      315                      320

CAG  CTA  CTT  GAG  CTT  TCT  GGA  GTA  GGC  AAC  CCC  GAT  GTA  CTG  GCA  GCC    1008
Gln  Leu  Leu  Glu  Leu  Ser  Gly  Val  Gly  Asn  Pro  Asp  Val  Leu  Ala  Ala
                         325                      330                      335

GCC  GCC  GTG  CCG  CTC  AAA  TTG  GCG  TCT  CCA  AAC  GTT  GGC  AAA  AAC  ATG    1056
Ala  Ala  Val  Pro  Leu  Lys  Leu  Ala  Ser  Pro  Asn  Val  Gly  Lys  Asn  Met
               340                      345                      350

CAA  GAG  CAA  ACC  AAG  AAC  ACC  CTC  TGG  TTC  GAT  CCC  GTC  AAC  ACC  GAG    1104
Gln  Glu  Gln  Thr  Lys  Asn  Thr  Leu  Trp  Phe  Asp  Pro  Val  Asn  Thr  Glu
          355                      360                      365

TTC  GAT  GGT  TCT  GGA  CCA  CCC  AAC  GCC  ATC  TCT  TTC  CCG  AAT  GTC  GAT    1152
Phe  Asp  Gly  Ser  Gly  Pro  Pro  Asn  Ala  Ile  Ser  Phe  Pro  Asn  Val  Asp
370                      375                      380

CAG  TTG  TTC  AGG  AAT  AAC  AGC  GCC  ACC  ATG  TAC  AAG  AAC  ATC  ATG  TCT    1200
Gln  Leu  Phe  Arg  Asn  Asn  Ser  Ala  Thr  Met  Tyr  Lys  Asn  Ile  Met  Ser
385                      390                      395                      400

GGC  CTC  AAG  CAA  TAC  TCA  GAA  GAC  CTG  GCC  GCT  ACC  GGC  ACG  GTG  ACC    1248
Gly  Leu  Lys  Gln  Tyr  Ser  Glu  Asp  Leu  Ala  Ala  Thr  Gly  Thr  Val  Thr
                         405                      410                      415

AAC  GCC  ACA  GCC  ACC  CAC  CAG  ATC  CTC  GAA  GCA  CAG  GTC  GAC  AAC  CTC    1296
Asn  Ala  Thr  Ala  Thr  His  Gln  Ile  Leu  Glu  Ala  Gln  Val  Asp  Asn  Leu
               420                      425                      430

TGG  CAC  AAC  CTT  GTA  GGC  GCC  GCC  GAA  ATC  TTC  TTC  GTG  ACA  TCA  CCC    1344
Trp  His  Asn  Leu  Val  Gly  Ala  Ala  Glu  Ile  Phe  Phe  Val  Thr  Ser  Pro
          435                      440                      445

GCC  ACC  GGC  CAA  GTC  GGC  GTC  GAC  CTC  TGG  AAC  CTG  ATC  GTT  TTG  TCG    1392
Ala  Thr  Gly  Gln  Val  Gly  Val  Asp  Leu  Trp  Asn  Leu  Ile  Val  Leu  Ser
450                      455                      460

CGT  GGC  TAT  GTG  CAC  ATC  ACC  TCA  AAC  TCC  TCA  TGG  GAT  CAC  CCA  GAA    1440
Arg  Gly  Tyr  Val  His  Ile  Thr  Ser  Asn  Ser  Ser  Trp  Asp  His  Pro  Glu
465                      470                      475                      480

ATC  GAG  CCT  TCC  TAC  TTC  GGT  CAC  CAA  TTC  GAC  CTC  GAC  GTC  CAA  CTA    1488
Ile  Glu  Pro  Ser  Tyr  Phe  Gly  His  Gln  Phe  Asp  Leu  Asp  Val  Gln  Leu
                         485                      490                      495

GCA  GCG  ACC  AAG  CAG  TCG  CGC  GAA  GTC  TTC  CAG  ACC  GAC  CCT  CTA  GCT    1536
Ala  Ala  Thr  Lys  Gln  Ser  Arg  Glu  Val  Phe  Gln  Thr  Asp  Pro  Leu  Ala
               500                      505                      510

CCT  CTC  GTC  AGC  GCT  GAG  ACT  TTC  CCG  GGC  CTT  GAA  GCC  GTG  CCG  CAA    1584
Pro  Leu  Val  Ser  Ala  Glu  Thr  Phe  Pro  Gly  Leu  Glu  Ala  Val  Pro  Gln
          515                      520                      525

GGC  GCA  GAA  GAT  CAG  GTC  TGG  GAG  CAG  TGG  GTC  AAA  GCC  ACC  TTC  ACC    1632
Gly  Ala  Glu  Asp  Gln  Val  Trp  Glu  Gln  Trp  Val  Lys  Ala  Thr  Phe  Thr
```

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     |     | 530 |     |     |     | 535 |     |     |     | 540 |     |     |      |
| TCT | GTC | TGG | CAC | TAC | ATC | GCA | ACC | TTG | GGT | ATG | ATG | AAG | GAG | GAA | CTT | 1680 |
| Ser | Val | Trp | His | Tyr | Ile | Ala | Thr | Leu | Gly | Met | Met | Lys | Glu | Glu | Leu |      |
| 545 |     |     |     |     | 550 |     |     |     |     | 555 |     |     |     |     | 560 |      |
| GGA | GGC | GTC | GTG | GAC | AGC | AGA | TTG | AAG | GTC | TAC | GGT | ATT | GAG | AAT | GTG | 1728 |
| Gly | Gly | Val | Val | Asp | Ser | Arg | Leu | Lys | Val | Tyr | Gly | Ile | Glu | Asn | Val |      |
|     |     |     |     | 565 |     |     |     |     | 570 |     |     |     |     | 575 |     |      |
| CGT | GCT | GTG | GAT | GCT | AGC | GTG | TTG | CCG | ATT | CAG | CTT | TCG | GCG | CAT | CTT | 1776 |
| Arg | Ala | Val | Asp | Ala | Ser | Val | Leu | Pro | Ile | Gln | Leu | Ser | Ala | His | Leu |      |
|     |     |     | 580 |     |     |     |     | 585 |     |     |     |     | 590 |     |     |      |
| AGT | TCT | TCG | CTG | TAT | GGC | ATT | GCT | GAG | AAG | GCT | GCG | AAG | ATG | ATC | AAG | 1824 |
| Ser | Ser | Ser | Leu | Tyr | Gly | Ile | Ala | Glu | Lys | Ala | Ala | Lys | Met | Ile | Lys |      |
|     |     | 595 |     |     |     |     | 600 |     |     |     |     | 605 |     |     |     |      |
| GAG | GAT | CAG | AGG | GCG |     |     |     |     |     |     |     |     |     |     |     | 1839 |
| Glu | Asp | Gln | Arg | Ala |     |     |     |     |     |     |     |     |     |     |     |      |
| 610 |     |     |     |     |     |     |     |     |     |     |     |     |     |     |     |      |

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:4:

| Ala | Glu | Ser | Ala | His | Ala | Ile | Thr | Ala | Asp | Val | Ser | Gln | Val |
|-----|-----|-----|-----|-----|-----|-----|-----|-----|-----|-----|-----|-----|-----|
| 1   |     |     |     | 5   |     |     |     |     | 10  |     |     |     |     |

( 2 ) INFORMATION FOR SEQ ID NO:5:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:5:

| Ala | Thr | Phe | Thr | Ser | Val | Trp | His | Tyr | Ile | Ala | Thr | Leu | Gly | Met | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Lys ( 2 ) INFORMATION FOR SEQ ID NO:6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:6:

| Thr | Gln | Tyr | Asp | Leu | Leu | Pro | Gly | Leu | Thr | Gly | Asp | Asp | Ser | Trp | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Asp | Ala | Leu | Asn | Glu | Ile | Met | Leu | Ser | Ile | Glu | Asp |
|-----|-----|-----|-----|-----|-----|-----|-----|-----|-----|-----|-----|-----|
|     |     |     | 20  |     |     |     |     | 25  |     |     |     |     |

( 2 ) INFORMATION FOR SEQ ID NO:7:

( i ) SEQUENCE CHARACTERISTICS:
        ( A ) LENGTH: 54 amino acids (B) TYPE: amino acid
(C) STRANDEDNESS: single
(D) TOPOLOGY: linear (ii) MOLECULE TYPE: None (xi) SEQUENCE DESCRIPTION: SEQ ID NO:7:

| Gln | Tyr | Ser | Glu | Asp | Leu | Ala | Ala | Thr | Gly | Thr | Val | Thr | Xaa | Ala | Thr |
|---|---|---|---|---|---|---|---|---|---|---|---|---|---|---|---|
| 1 | | | | 5 | | | | | 10 | | | | | 15 | |
| Ala | Thr | His | Gln | Ile | Leu | Glu | Ala | Gln | Val | Asp | Asn | Leu | Trp | His | Asn |
| | | | 20 | | | | | 25 | | | | | 30 | | |
| Leu | Val | Gly | Ala | Ala | Glu | Ile | Phe | Phe | Val | Thr | Ser | Pro | Ala | Thr | Gly |
| | | | 35 | | | | 40 | | | | | 45 | | | |
| Gln | Val | Gly | Val | Asp | Leu | | | | | | | | | | |
| 50 | | | | | | | | | | | | | | | |

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:8:

GCNCAYGCNA THACNGCNGA YGT        23

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

GAGGACTTAC GGACAAGCCT T        21

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:10:

CCACCATGTA CAAACCCATC GCGC        24

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

CATDATYTCR TTNAGNGCRT CRAA        24

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( x i ) SEQUENCE DESCRIPTION: SEQ ID NO:12:

TTRTGCCANA GRTTRTCNAC 20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATCAACCTGT GCTTCGAGGA T 21

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCCTTAATTA ACGCTCATCA CGCCCTCTGA TCCTC 35

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:15:

Ala Glu Ser Ala His Ala Ile Thr Ala Asp Val Ser Gln Val
1               5                   10

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:16:

Asp Val Arg Thr Tyr Gly Gln Ala Phe Glu
1               5                   10

( 2 ) INFORMATION FOR SEQ ID NO:17:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:17:

Ser Thr Ser Val Pro Trp Gln Xaa Asn Thr Gly Leu Leu Leu Val Ala
1               5                   10                  15

Gly Lys ( 2 ) INFORMATION FOR SEQ ID NO:18:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:18:

```
Val  Ala  Asp  Phe  Ala  Ala  Gly  Ile  Thr  Thr  Gly  Ala  Thr  Met  Ile  Pro
 1              5                        10                            15

Asn  Met  Leu  Glu  Ala  Asn  Glu  Ser  Gln  Xaa  Arg  Ser  Ser
              20                        25
```

( 2 ) INFORMATION FOR SEQ ID NO:19:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:19:

```
Glu  Val  Leu  Leu  Ala  Gly  Gly  Ser  Leu  Gln  Ser
 1              5                        10
```

( 2 ) INFORMATION FOR SEQ ID NO:20:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:20:

```
Asn  Thr  Leu  Trp  Phe  Asp  Pro  Val  Asn  Thr  Glu  Phe  Asp  Gly  Ser  Gly
 1              5                        10                            15

Pro  Pro  Asn  Ala  Ile  Ser  Phe  Pro  Asn  Val  Asp  Gln  Leu  Phe  Arg  Xaa
              20                        25                            30

Asn  Tyr  Ala  Thr
              35
```

( 2 ) INFORMATION FOR SEQ ID NO:21:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:21:

```
Asp  His  Pro  Glu  Ile  Glu  Pro  Ser  Tyr  Phe  Gly  His  Gln  Phe
 1              5                        10
```

( 2 ) INFORMATION FOR SEQ ID NO:22:

( i ) SEQUENCE CHARACTERISTICS:
        ( A ) LENGTH: 21 amino acids
        ( B ) TYPE: amino acid (C) STRANDEDNESS: single
(D) TOPOLOGY: linear (ii) MOLECULE TYPE: None (xi) SEQUENCE DESCRIPTION: SEQ ID NO:22:

```
Val  Tyr  Gly  Ile  Glu  Asn  Val  Xaa  Ala  Val  Asp  Ala  Ser  Val  Leu  Pro
 1              5                        10                       15
Ile  Gln  Leu  Ser  Ala
              20
```

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:23:

GAGCTCGAGG AATTCTTACA AACCTTCAAC     30

(2) INFORMATION FOR SEQ ID NO:24:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:24:

TTAATTAAGG TACCTGAATT TAAATGGTGA AGAGATAGAT ATCCAAG     47

(2) INFORMATION FOR SEQ ID NO:25:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:25:

TCACCATTTA AATTCAGGTA CCTTAATTAA ATTCCTTGTT GGAAGCGTCG A     51

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:26:

TGGTATGCAT AAGCTTGAAT TCAGGTAAAC AAGATATAAT TT     42

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:27:

CCACCATGTA CAAACCCATC GCGC     24

(2) INFORMATION FOR SEQ ID NO:28:

(i) SEQUENCE CHARACTERISTICS:
  (A) LENGTH: 35 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:28:

CCCTTAATTA ACGCTCATCA CGCCCTCTGA TCCTC    35

(2) INFORMATION FOR SEQ ID NO:29:

(i) SEQUENCE CHARACTERISTICS:
    (A) LENGTH: 612 amino acids
    (B) TYPE: amino acid
    (C) STRANDEDNESS: single
    (D) TOPOLOGY: linear (xi) SEQUENCE DESCRIPTION: SEQ ID NO:29:

```
Tyr Lys Pro Ile Ala Leu Ser Thr Leu Leu Ala Val Ala Ser Gln Ala
 1               5                  10                  15

Leu Pro His Gln Ser Arg Ala Glu Ser Ala His Ala Ile Thr Ala Asp
             20                  25                  30

Val Ser Gln Val Ser Asn Lys Thr Phe Asp Tyr Ile Val Cys Gly Gly
         35                  40                  45

Gly Leu Thr Gly Leu Val Val Ala Ser Arg Leu Ser Glu Asp Pro Asn
     50                  55                  60

Ile Ser Val Leu Val Ile Glu Gly Gly Asn Asp His Glu Asp Pro
65                  70                  75                  80

Arg Val Asn Asp Val Arg Thr Tyr Gly Gln Ala Phe Glu Thr Glu Leu
                 85                  90                  95

Asp Tyr Gly Leu Lys Ser Thr Ser Val Pro Trp Gln Asn Asn Thr Gly
             100                 105                 110

Leu Leu Leu Val Ala Gly Lys Thr Leu Gly Gly Ser Gly Ser Ile Asn
             115                 120                 125

Gly Ala Ser Trp Thr Lys Gly Asp Lys Thr Gln Tyr Asp Leu Leu Pro
     130                 135                 140

Gly Leu Thr Gly Asp Asp Ser Trp Ser Phe Asp Ala Leu Asn Glu Ile
145                 150                 155                 160

Met Leu Ser Ile Glu Asp Phe His Thr Pro Thr Glu Asp Gln Val Ala
                 165                 170                 175

Lys Gly Ala Ala Phe Glu Gly Glu Phe His Gly Arg Glu Gly Asn Val
             180                 185                 190

Gln Val Ser Phe Pro Ala Gly Met Phe Gly Ser Ile Gln Gln Pro Ala
         195                 200                 205

Leu Glu Ala Ser Ala Leu Val Trp Lys Gly Met Lys Lys Val Ala Asp
     210                 215                 220

Phe Ala Ala Gly Ile Thr Thr Gly Ala Thr Met Ile Pro Asn Met Leu
225                 230                 235                 240

Glu Ala Asn Glu Ser Gln Asn Arg Ser Ser Pro Phe Thr Val Tyr Ala
                 245                 250                 255

Lys Gln Gln Thr Gln Glu Arg Asp Asn Phe Ile Ile Leu Thr Gly His
             260                 265                 270

Arg Val Ile Ser Leu Asn Trp Arg Glu Gly Ser Glu Met Ile Ala Asp
         275                 280                 285

Gly Val Ser Phe Gln Ala Cys Arg Asp Cys Lys Ile His Lys Ala Lys
     290                 295                 300
```

| Thr | Lys | Arg | Glu | Val | Leu | Leu | Ala | Gly | Gly | Ser | Leu | Gln | Ser | Pro | Gln |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |
| Leu | Leu | Glu | Leu | Ser | Gly | Val | Gly | Asn | Pro | Asp | Val | Leu | Ala | Ala | Ala |
|     |     |     |     | 325 |     |     |     |     | 330 |     |     |     |     | 335 |     |
| Ala | Val | Pro | Leu | Lys | Leu | Ala | Ser | Pro | Asn | Val | Gly | Lys | Asn | Met | Gln |
|     |     |     | 340 |     |     |     |     | 345 |     |     |     |     | 350 |     |     |
| Glu | Gln | Thr | Lys | Asn | Thr | Leu | Trp | Phe | Asp | Pro | Val | Asn | Thr | Glu | Phe |
|     |     | 355 |     |     |     |     | 360 |     |     |     |     | 365 |     |     |     |
| Asp | Gly | Ser | Gly | Pro | Pro | Asn | Ala | Ile | Ser | Phe | Pro | Asn | Val | Asp | Gln |
|     | 370 |     |     |     |     | 375 |     |     |     |     | 380 |     |     |     |     |
| Leu | Phe | Arg | Asn | Asn | Ser | Ala | Thr | Met | Tyr | Lys | Asn | Ile | Met | Ser | Gly |
| 385 |     |     |     |     | 390 |     |     |     |     | 395 |     |     |     |     | 400 |
| Leu | Lys | Gln | Tyr | Ser | Glu | Asp | Leu | Ala | Ala | Thr | Gly | Thr | Val | Thr | Asn |
|     |     |     |     | 405 |     |     |     |     | 410 |     |     |     |     | 415 |     |
| Ala | Thr | Ala | Thr | His | Gln | Ile | Leu | Glu | Ala | Gln | Val | Asp | Asn | Leu | Trp |
|     |     |     | 420 |     |     |     |     | 425 |     |     |     |     | 430 |     |     |
| His | Asn | Leu | Val | Gly | Ala | Ala | Glu | Ile | Phe | Phe | Val | Thr | Ser | Pro | Ala |
|     |     | 435 |     |     |     |     | 440 |     |     |     |     | 445 |     |     |     |
| Thr | Gly | Gln | Val | Gly | Val | Asp | Leu | Trp | Asn | Leu | Ile | Val | Leu | Ser | Arg |
|     | 450 |     |     |     |     | 455 |     |     |     |     | 460 |     |     |     |     |
| Gly | Tyr | Val | His | Ile | Thr | Ser | Asn | Ser | Ser | Trp | Asp | His | Pro | Glu | Ile |
| 465 |     |     |     |     | 470 |     |     |     |     | 475 |     |     |     |     | 480 |
| Glu | Pro | Ser | Tyr | Phe | Gly | His | Gln | Phe | Asp | Leu | Asp | Val | Gln | Leu | Ala |
|     |     |     |     | 485 |     |     |     |     | 490 |     |     |     |     | 495 |     |
| Ala | Thr | Lys | Gln | Ser | Arg | Glu | Val | Phe | Gln | Thr | Asp | Pro | Leu | Ala | Pro |
|     |     |     | 500 |     |     |     |     | 505 |     |     |     |     | 510 |     |     |
| Leu | Val | Ser | Ala | Glu | Thr | Phe | Pro | Gly | Leu | Glu | Ala | Val | Pro | Gln | Gly |
|     |     | 515 |     |     |     |     | 520 |     |     |     |     | 525 |     |     |     |
| Ala | Glu | Asp | Gln | Val | Trp | Glu | Gln | Trp | Val | Lys | Ala | Thr | Phe | Thr | Ser |
|     | 530 |     |     |     |     | 535 |     |     |     |     | 540 |     |     |     |     |
| Val | Trp | His | Tyr | Ile | Ala | Thr | Leu | Gly | Met | Met | Lys | Glu | Glu | Leu | Gly |
| 545 |     |     |     |     | 550 |     |     |     |     | 555 |     |     |     |     | 560 |
| Gly | Val | Val | Asp | Ser | Arg | Leu | Lys | Val | Tyr | Gly | Ile | Glu | Asn | Val | Arg |
|     |     |     |     | 565 |     |     |     |     | 570 |     |     |     |     | 575 |     |
| Ala | Val | Asp | Ala | Ser | Val | Leu | Pro | Ile | Gln | Leu | Ser | Ala | His | Leu | Ser |
|     |     |     | 580 |     |     |     |     | 585 |     |     |     |     | 590 |     |     |
| Ser | Ser | Leu | Tyr | Gly | Ile | Ala | Glu | Lys | Ala | Ala | Lys | Met | Ile | Lys | Glu |
|     |     | 595 |     |     |     |     | 600 |     |     |     |     | 605 |     |     |     |
| Asp | Gln | Arg | Ala |     |     |     |     |     |     |     |     |     |     |     |     |
|     | 610 |     |     |     |     |     |     |     |     |     |     |     |     |     |     |

( 2 ) INFORMATION FOR SEQ ID NO:30:

( i ) SEQUENCE CHARACTERISTICS:
        ( A ) LENGTH: 604 amino acids
        ( B ) TYPE: amino acid
        ( C ) STRANDEDNESS: single
        ( D ) TOPOLOGY: linear ( x i ) SEQUENCE DESCRIPTION: SEQ ID NO:30:

| Met | Gln | Thr | Leu | Leu | Val | Ser | Ser | Leu | Val | Val | Ser | Leu | Ala | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | Pro | His | Tyr | Ile | Arg | Ser | Asn | Gly | Ile | Glu | Ala | Ser | Leu | Leu | Thr |
|     |     |     | 20  |     |     |     |     | 25  |     |     |     |     | 30  |     |     |
| Asp | Pro | Lys | Asp | Val | Ser | Gly | Arg | Thr | Val | Asp | Tyr | Ile | Ile | Ala | Gly |
|     |     | 35  |     |     |     |     | 40  |     |     |     |     | 45  |     |     |     |

| | | | | | | | | | | | | | | |
|---|---|---|---|---|---|---|---|---|---|---|---|---|---|---|
| Gly | Gly | Leu | Thr | Gly | Leu | Thr | Thr | Ala | Ala | Arg | Leu | Thr | Glu | Asn | Pro |
| | 50 | | | | 55 | | | | | 60 | | | | |
| Asn | Ile | Ser | Val | Leu | Val | Ile | Glu | Ser | Gly | Ser | Tyr | Glu | Ser | Asp | Arg |
| 65 | | | | | 70 | | | | 75 | | | | | 80 |
| Gly | Pro | Ile | Ile | Glu | Asp | Leu | Asn | Ala | Tyr | Gly | Asp | Ile | Phe | Gly | Ser |
| | | | | 85 | | | | | 90 | | | | | 95 |
| Ser | Val | Asp | His | Ala | Tyr | Glu | Thr | Val | Glu | Leu | Ala | Thr | Asn | Asn | Gln |
| | | | 100 | | | | | 105 | | | | | 110 | |
| Thr | Ala | Leu | Ile | Arg | Ser | Gly | Asn | Gly | Leu | Gly | Gly | Ser | Thr | Leu | Val |
| | | | 115 | | | | 120 | | | | | 125 | | |
| Asn | Gly | Gly | Thr | Trp | Thr | Arg | Pro | His | Lys | Ala | Gln | Val | Asp | Ser | Trp |
| | | 130 | | | | 135 | | | | | 140 | | | | |
| Glu | Thr | Val | Phe | Gly | Asn | Gly | Trp | Asn | Trp | Asp | Asn | Val | Ala | Ala |
| 145 | | | | | 150 | | | | 155 | | | | | 160 |
| Tyr | Ser | Leu | Gln | Ala | Glu | Arg | Ala | Arg | Ala | Pro | Asn | Ala | Lys | Gln | Ile |
| | | | | 165 | | | | | 170 | | | | | 175 | |
| Ala | Ala | Gly | His | Tyr | Phe | Asn | Ala | Ser | Cys | His | Gly | Val | Asn | Gly | Thr |
| | | | 180 | | | | | 185 | | | | | 190 | | |
| Val | His | Ala | Gly | Pro | Arg | Asp | Thr | Gly | Asp | Asp | Tyr | Ser | Pro | Ile | Val |
| | | 195 | | | | | 200 | | | | | 205 | | | |
| Lys | Ala | Leu | Met | Ser | Ala | Val | Glu | Asp | Arg | Gly | Val | Pro | Thr | Lys | Lys |
| | 210 | | | | | 215 | | | | | 220 | | | | |
| Asp | Phe | Gly | Cys | Gly | Asp | Pro | His | Gly | Val | Ser | Met | Phe | Pro | Asn | Thr |
| 225 | | | | | 230 | | | | | 235 | | | | | 240 |
| Leu | His | Glu | Asp | Gln | Val | Arg | Ser | Asp | Ala | Ala | Arg | Glu | Trp | Leu | Leu |
| | | | | 245 | | | | | 250 | | | | | 255 | |
| Pro | Asn | Tyr | Gln | Arg | Pro | Asn | Leu | Gln | Val | Leu | Thr | Gly | Gln | Tyr | Val |
| | | | | 260 | | | | 265 | | | | | 270 | | |
| Gly | Lys | Val | Leu | Leu | Ser | Gln | Asn | Gly | Thr | Thr | Pro | Arg | Ala | Val | Gly |
| | | | 275 | | | | | 280 | | | | | 285 | | |
| Val | Glu | Phe | Gly | Thr | His | Lys | Gly | Asn | Thr | His | Asn | Val | Tyr | Ala | Lys |
| | 290 | | | | | 295 | | | | | 300 | | | | |
| His | Glu | Val | Leu | Leu | Ala | Ala | Gly | Ser | Ala | Val | Ser | Pro | Thr | Ile | Leu |
| 305 | | | | | 310 | | | | | 315 | | | | | 320 |
| Glu | Tyr | Ser | Gly | Ile | Gly | Met | Lys | Ser | Ile | Leu | Glu | Pro | Leu | Gly | Ile |
| | | | | 325 | | | | | 330 | | | | | 335 | |
| Asp | Thr | Val | Val | Asp | Leu | Pro | Val | Gly | Leu | Asn | Leu | Gln | Asp | Gln | Thr |
| | | | 340 | | | | | 345 | | | | | 350 | | |
| Thr | Ala | Thr | Val | Arg | Ser | Arg | Ile | Thr | Ser | Ala | Gly | Ala | Gly | Gln | Gly |
| | | 355 | | | | | 360 | | | | | 365 | | | |
| Gln | Ala | Ala | Trp | Phe | Ala | Thr | Phe | Asn | Glu | Thr | Phe | Gly | Asp | Tyr | Ser |
| | 370 | | | | | 375 | | | | | 380 | | | | |
| Glu | Lys | Ala | His | Glu | Leu | Leu | Asn | Thr | Lys | Leu | Glu | Gln | Trp | Ala | Glu |
| 385 | | | | | 390 | | | | | 395 | | | | | 400 |
| Glu | Ala | Val | Ala | Arg | Gly | Gly | Phe | His | Asn | Thr | Thr | Ala | Leu | Leu | Ile |
| | | | | 405 | | | | | 410 | | | | | 415 | |
| Gln | Tyr | Glu | Asn | Tyr | Arg | Asp | Trp | Ile | Val | Asn | His | Asn | Val | Ala | Tyr |
| | | | 420 | | | | | 425 | | | | | 430 | | |
| Ser | Glu | Leu | Phe | Leu | Asp | Thr | Ala | Gly | Val | Ala | Ser | Phe | Asp | Val | Trp |
| | | 435 | | | | | 440 | | | | | 445 | | | |
| Asp | Leu | Leu | Pro | Phe | Thr | Arg | Gly | Tyr | Val | His | Ile | Leu | Asp | Lys | Asp |
| | 450 | | | | | 455 | | | | | 460 | | | | |
| Pro | Tyr | Leu | His | His | Phe | Ala | Tyr | Asp | Pro | Gln | Tyr | Phe | Leu | Asn | Glu |

|  | 465 |  |  |  | 470 |  |  |  |  | 475 |  |  |  | 480 |  |
|---|---|---|---|---|---|---|---|---|---|---|---|---|---|---|---|
| Leu | Asp | Leu | Leu | Gly<br>485 | Gln | Ala | Ala | Ala | Thr<br>490 | Gln | Leu | Ala | Arg | Asn<br>495 | Ile |
| Ser | Asn | Ser | Gly<br>500 | Ala | Met | Gln | Thr | Tyr<br>505 | Phe | Ala | Gly | Glu | Thr<br>510 | Ile | Pro |
| Gly | Asp | Asn<br>515 | Leu | Ala | Tyr | Asp | Ala<br>520 | Asp | Leu | Ser | Ala | Trp<br>525 | Thr | Glu | Tyr |
| Ile | Pro<br>530 | Tyr | His | Phe | Arg | Pro<br>535 | Asn | Tyr | His | Gly | Val<br>540 | Gly | Thr | Cys | Ser |
| Met<br>545 | Met | Pro | Lys | Glu | Met<br>550 | Gly | Gly | Val | Val | Asp<br>555 | Asn | Ala | Ala | Arg | Val<br>560 |
| Tyr | Gly | Val | Gln | Gly<br>565 | Leu | Arg | Val | Ile | Asp<br>570 | Gly | Ser | Ile | Pro | Pro<br>575 | Thr |
| Gln | Met | Ser | Ser<br>580 | His | Val | Met | Thr | Val<br>585 | Phe | Tyr | Ala | Met | Ala<br>590 | Leu | Lys |
| Ile | Ser | Asp<br>595 | Ala | Ile | Leu | Glu | Asp<br>600 | Tyr | Ala | Ser | Met |  |  |  |  |

What is claimed is:

1. An isolated nucleic acid fragment comprising a nucleic acid sequence encoding a polypeptide having glucose oxidase activity with more than about 75% maximum activity between about pH 5 to about pH 8, determined at 30° C. with D-glucose as substrate, wherein the nucleic acid sequence is selected from the group consisting of:

(a) a nucleic acid sequence, obtained from a Cladosporium strain, encoding a polypeptide having an amino acid sequence which has at least 70% identity with the amino acid sequence of SEQ ID NO:1;

(b) a nucleic acid sequence, obtained from a Cladosporium strain, which hybridizes under medium stringency conditions with one or more of (i) the nucleic acid sequences of SEQ ID NO;2 and SEQ ID NO:3, and (ii) either of their complementary strands, wherein the medium stringency conditions are defined by prehybridization and hybridization at 42° C. in 5× SSPE, 0.3% SDS, 200 μg/ml sheared and denatured salmon sperm DNA, and 35% formamide, and wash conditions at 60° C. for 30 minutes in 0.2× SSC, 0.1% SDS;

(c) a nucleic acid sequence which encodes SEQ ID NO:1; and (d) a subsequence of (a), (b), or (c), wherein the subsequence encodes a polypeptide having glucose oxidase activity with more than about 75% maximum activity between about pH 5 to about pH 8, determined at 30° C. with D-glucose as substrate.

2. The isolated nucleic acid fragment of claim 1, wherein the nucleic acid sequence, obtained from a Cladosporium strain, encodes a polypeptide having an amino acid sequence which has at least 70% identity with the amino acid sequence of SEQ ID NO:1.

3. The isolated nucleic acid fragment of claim 2, wherein the nucleic acid sequence encodes a polypeptide having an amino acid sequence which has at least 80% identity with the amino acid sequence of SEQ ID NO:1.

4. The isolated nucleic acid fragment of claim 3, wherein the nucleic acid sequence encodes a polypeptide having an amino acid sequence which has at least 90% identity with the amino acid sequence of SEQ ID NO:1.

5. The isolated nucleic acid fragment of claim 4, wherein the nucleic acid sequence encodes a polypeptide having an amino acid sequence which has at least 95% identity with the amino acid sequence of SEQ ID NO:1.

6. The isolated nucleic acid fragment of claim 1, wherein the nucleic acid sequence encodes a polypeptide having the amino acid sequence of SEQ ID NO:1; or a subsequence thereof which encodes a polypeptide having glucose oxidase activity with more than about 75% maximum activity between about pH 5 to about pH 8, determined at 30° C. with D-glucose as substrate.

7. The isolated nucleic acid fragment of claim 6, wherein the nucleic acid sequence encodes a polypeptide having the amino acid sequence of SEQ ID NO:1.

8. The isolated nucleic acid fragment of claim 1, wherein the nucleic acid sequence encodes a polypeptide having amino acids 24 to 613 of SEQ ID NO:1.

9. The isolated nucleic acid fragment of claim 1, wherein the nucleic acid sequence is SEQ ID NO:2 or SEQ ID NO:3.

10. The Isolated nucleic acid fragment of claim 1, wherein the nucleic acid sequence comprises nucleotides 419 to 2189 of SEQ ID NO:2.

11. The isolated nucleic acid fragment of claim 1, wherein the nucleic acid sequence, obtained from a Cladosporium strain, hybridizes under medium stringency conditions to one or more of (i) the nucleic acid sequences of SEQ ID NO:2 and SEQ ID NO:3 and (ii) either of their complementary strands, wherein the medium stringency conditions are defined by prehybridization and hybridization at 42° C. in 5× SSPE, 0.3% SDS, 200 μg/ml sheared and denatured salmon sperm DNA, and 35% formamide, and wash conditions at 60° C. for 30 minutes in 0.2× SSC, 0.1% SDS.

12. The isolated nucleic acid fragment of claim 11, wherein the Cladosporium strain is a *Cladosporium oxysporum* strain.

13. The isolated nucleic acid fragment of claim 1, wherein the nucleic acid sequence is contained in the plasmid pGOX4A which is contained in *Escherichia coli* NRRL B-21628 and plasmid pGOX6A which is contained in *Escherichia coli* NRRL B-21629.

14. A nucleic acid construct comprising the isolated nucleic acid fragment of claim 1, wherein the nucleic acid sequence is operably linked to one or more control sequences which direct the production of the polypeptide in a suitable expression host.

15. A recombinant expression vector comprising the nucleic acid construct of claim 14.

16. The vector of claim 15, further comprising a selectable marker.

17. A recombinant host cell comprising the nucleic acid construct of claim 14.

18. The recombinant host cell of claim 17, wherein the nucleic acid construct comprises SEQ ID NO:2 or SEQ ID NO:3; or a subsequence thereof which encodes a polypeptide having glucose oxidase activity with more than about 75% maximum activity between about pH 5 to about pH 8, determined a 30° C. with D-glucose as substrate.

19. The recombinant host cell of claim 17, wherein the nucleic acid construct comprises nucleotides 419 to 2189 of SEQ ID NO:2.

20. The recombinant host cell of claim 17, wherein the nucleic acid construct is contained on a vector.

21. The recombinant host cell of claim 17, wherein the nucleic acid construct upon introduction into the cell integrates into the host cell genome.

22. The recombinant host cell of claim 17, wherein the host cell is a yeast or filamentous fungal cell.

23. A method for producing a polypeptide having glucose oxidase activity comprising (a) cultivating the host cell of claim 17 under conditions suitable for the production of the polypeptide; and (b) recovering the polypeptide.

24. The method of claim 23, wherein the polypeptide having glucose activity is encoded by SEQ ID NO:2 or SEQ ID NO:3; or a subsequence thereof which encodes a polypeptide having glucose oxidase activity with more than about 75% maximum activity between about pH 5 to about pH 8, determined at 30° C. with D-glucose as substrate.

25. The method of claim 23, wherein the polypeptlde having glucose activity is encoded by nucleic acid sequence comprising nucleotides 419 to 2189 of SEQ ID NO:2.

* * * * *

UNITED STATES PATENT AND TRADEMARK OFFICE
CERTIFICATE OF CORRECTION

PATENT NO. : 5,879,921

DATED : March 9, 1999

INVENTOR(S) : Cherry et al.

It is certified that error appears in the above-identified patent and that said Letters Patent is hereby corrected as shown below:

Col. 59, line 33: delete "Cladosporium" and insert -- *Cladosporium* --
Col. 59, line 37: delete "Cladosporium" and insert -- *Cladosporium* --
Col. 59, line 41: delete "SEQ ID NO;2" and insert -- SEQ ID NO:2 --
Col. 59, line 56: delete "Cladosporium" and insert -- *Cladosporium* --
Col. 60, line 44: delete "Isolated" and insert -- isolated --
Col. 60, line 48: delete "Cladosporium" and insert -- *Cladosporium* --
Col. 60, line 58: delete "Cladosporium" and insert -- *Cladosporium* --
Col. 62, line 15: delete "polypeptlde" and insert -- polypeptide --

Signed and Sealed this

Fourteenth Day of December, 1999

Attest:

Q. TODD DICKINSON

*Attesting Officer*

*Acting Commissioner of Patents and Trademarks*